US008426138B2

(12) United States Patent
Blau et al.

(10) Patent No.: US 8,426,138 B2
(45) Date of Patent: Apr. 23, 2013

(54) DETECTION OF SUB-CELLULAR COMPARTMENT LOCALIZATION OF A MOLECULE USING A REDUCED AFFINITY ENZYME COMPLEMENTATION REPORTER SYSTEM

(75) Inventors: Helen M. Blau, Menlo Park, CA (US); Mark Morris Hammer, Gainesville, FL (US); Tom Wehrman, Fremont, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 832 days.

(21) Appl. No.: 11/964,411

(22) Filed: Dec. 26, 2007

(65) Prior Publication Data

US 2010/0285451 A1 Nov. 11, 2010

Related U.S. Application Data

(60) Provisional application No. 60/877,260, filed on Dec. 26, 2006.

(51) Int. Cl.
*G01N 33/573* (2006.01)
*C12Q 1/34* (2006.01)
*C12Q 1/68* (2006.01)
*C12N 5/00* (2006.01)
*C12N 1/16* (2006.01)

(52) U.S. Cl.
USPC ....... 435/6.19; 435/325; 435/255.1; 435/7.21

(58) Field of Classification Search .................. None
See application file for complete search history.

(56) References Cited

U.S. PATENT DOCUMENTS

| 5,643,734 | A | * | 7/1997 | Henderson ............... 435/7.6 |
| 6,168,932 | B1 | | 1/2001 | Uckun et al. |
| 6,342,345 | B1 | | 1/2002 | Blau et al. |
| 6,828,099 | B2 | | 12/2004 | Michnick et al. |
| 6,893,827 | B1 | * | 5/2005 | Palmer et al. ............ 435/7.1 |
| 7,223,537 | B2 | | 5/2007 | Blau et al. |
| 2003/0175836 | A1 | | 9/2003 | Blau et al. |
| 2005/0287522 | A1 | | 12/2005 | Blau et al. |
| 2007/0275397 | A1 | | 11/2007 | Wehrman et al. |

FOREIGN PATENT DOCUMENTS

| EP | 1580195 A1 | 9/2005 |
| WO | 98/44350 | 10/1998 |
| WO | 00/71702 | 11/2000 |
| WO | 03/058197 | 7/2003 |
| WO | 2005/113838 | 12/2005 |
| WO | 2006108183 A2 | 10/2006 |
| WO | 2007/106456 | 9/2007 |

OTHER PUBLICATIONS

Parsons Human cancer, PTEN and the PI-3 kinase pathway.: Semin. Cell Dev Biol. Apr. 2004 :15 (2):171-6.*
Heyes et al (TGFβ receptor internalization into EEA1-enriched early endosomes: role in signaling to Smad2 (Journal of Cell Biology, vol. 158, No. 7, 1239-1249) Sep. 2002.*
Seet; et al., "Endofin, an Endosomal FYVE Domain Protein", The Journal of Biological Chemistry (2001), 276 (45):42445-42454.
Xiu-Huai Liu, et al., "Receptor-mediated uptake of an extracellular Bcl-xL fusion protein inhibits apoptosis," PNAS USA, Aug. 1999, vol. 96, 9563-9567.
Supplementary European Search Report, Mar. 4, 2010.
Mohler, William A.; et al., "Gene expression and cell fusion analyzed by lacZ complementation in mammalian cells", Proc. Natl. Acad. Sci., Oct. 29, 1996, 93(22):12423-7.
Wehrman, T. S.; et al., "A system for qualifying dynamic protein interactions defines a role for Herceptin in modulating ErbB2 interactions", PNAS, Dec. 12, 2006, 103(50):19063-8.
Wehrman, Tom S.; et al., "Enzymatic detection of protein translocation", Nature Methods, Jul. 2005, 2(7):521-7.
Wehrman, Thomas S.; et al., "Luminescent imagining of beta-galactosidase activity in living subjects using sequential reporter-enzyme luminescence", Nature Methods, Apr. 2006, 3(4):295-301.
Wehrman, Tom; et al., "Protein-protein interactions monitored in mammalian cells via complementation of beta-lactamase enzyme fragments", PNAS, Mar. 19, 2002, 99(6):3469-74.

* cited by examiner

*Primary Examiner* — Kagnew H Gebreyesus
(74) *Attorney, Agent, or Firm* — David J. Aston; Peters Verny, LLP

(57) ABSTRACT

Methods and compositions for detecting the sub-cellular localization of a molecule are provided. Aspects of the invention include detecting translocation of a cell-surface receptor to a sub-cellular compartment, e.g., the endosome, using a reduced affinity enzyme complementation reporter system. Also provided are systems and kits for use in practicing embodiments of the methods.

14 Claims, 8 Drawing Sheets

SEQUENCE LISTING

<160> NUMBER OF SEQ ID NOS: 8

<210> SEQ ID NO 1
<211> LENGTH: 52
<212> TYPE: PRT
<213> ORGANISM: Artificial Sequence
<220> FEATURE:
<223> OTHER INFORMATION: synthetic sequence

<400> SEQUENCE: 1

```
Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala Arg Pro
            20                  25                  30

Pro Phe Ala Ser Trp Arg Asn Ser Glu Glu Ala Arg Thr Asp Arg Pro
        35                  40                  45

Ser Gln Gln Leu
    50

<210> SEQ ID NO 2
<211> LENGTH: 52
<212> TYPE: PRT
<213> ORGANISM: Artificial Sequence
<220> FEATURE:
<223> OTHER INFORMATION: synthetic sequence

<400> SEQUENCE: 2

Met Gly Val Ile Thr Asp Ser Leu Ala Val Val Leu Gln Arg Arg Asp
1               5                   10                  15

Trp Glu Asn Pro Gly Val Thr Gln Leu Asn Arg Cys Ala Ala His Pro
            20                  25                  30

Pro Tyr Ala Ser Trp Arg Asn Ser Glu Glu Ala Arg Thr Asp Arg Pro
        35                  40                  45

Ser Gln Gln Leu
    50

<210> SEQ ID NO 3
<211> LENGTH: 52
<212> TYPE: PRT
<213> ORGANISM: Artificial Sequence
<220> FEATURE:
<223> OTHER INFORMATION: synthetic sequence

<400> SEQUENCE: 3

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Gln Glu Ala Arg Thr Asp Arg Pro
        35                  40                  45

Ser Gln Gln Leu
    50

<210> SEQ ID NO 4
<211> LENGTH: 52
<212> TYPE: PRT
<213> ORGANISM: Artificial Sequence
<220> FEATURE:
<223> OTHER INFORMATION: synthetic sequence

<400> SEQUENCE: 4

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asp Ser Glu Glu Ala Arg Thr Asp Arg Pro
        35                  40                  45

Ser Gln Gln Leu
    50
```

```
<210> SEQ ID NO 5
<211> LENGTH: 43
<212> TYPE: PRT
<213> ORGANISM: Artificial Sequence
<220> FEATURE:
<223> OTHER INFORMATION: synthetic sequence

<400> SEQUENCE: 5

Met Gly Val Ile Thr Asp Ser Leu Ala Val Val Leu Gln Arg Arg Asp
 1               5                  10                  15

Trp Glu Asn Pro Gly Val Thr Gln Leu Asn Arg Leu Ala Ala His Pro
            20                  25                  30

Pro Phe Ala Ser Trp Arg Asp Ser Glu Glu Ala
        35                  40

<210> SEQ ID NO 6
<211> LENGTH: 993
<212> TYPE: PRT
<213> ORGANISM: Artificial Sequence
<220> FEATURE:
<223> OTHER INFORMATION: synthetic sequence

<400> SEQUENCE: 6

Met Gly Val Ile Thr Asp Ser Leu Ala Val Val Ala Arg Thr Asp Arg
 1               5                  10                  15

Pro Ser Gln Gln Leu Arg Ser Leu Asn Gly Glu Trp Arg Phe Ala Trp
            20                  25                  30

Phe Pro Ala Pro Glu Ala Val Pro Glu Ser Trp Leu Glu Cys Asp Leu
        35                  40                  45

Pro Glu Ala Asp Thr Val Val Val Pro Ser Asn Trp Gln Met His Gly
    50                  55                  60

Tyr Asp Ala Pro Ile Tyr Thr Asn Val Thr Tyr Pro Ile Thr Val Asn
65                  70                  75                  80

Pro Pro Phe Val Pro Thr Glu Asn Pro Thr Gly Cys Tyr Ser Leu Thr
                85                  90                  95

Phe Asn Val Asp Glu Ser Trp Leu Gln Glu Gly Gln Thr Arg Ile Ile
            100                 105                 110

Phe Asp Gly Val Asn Ser Ala Phe His Leu Trp Cys Asn Gly Arg Trp
        115                 120                 125

Val Gly Tyr Gly Gln Asp Ser Arg Leu Pro Ser Glu Phe Asp Leu Ser
    130                 135                 140

Ala Phe Leu Arg Ala Gly Glu Asn Arg Leu Ala Val Met Val Leu Arg
145                 150                 155                 160

Trp Ser Asp Gly Ser Tyr Leu Glu Asp Gln Asp Met Trp Arg Met Ser
                165                 170                 175

Gly Ile Phe Arg Asp Val Ser Leu Leu His Lys Pro Thr Thr Gln Ile
            180                 185                 190

Ser Asp Phe His Val Ala Thr Arg Phe Asn Asp Asp Phe Ser Arg Ala
        195                 200                 205

Val Leu Glu Ala Glu Val Gln Met Cys Gly Glu Leu Arg Asp Tyr Leu
    210                 215                 220

Arg Val Thr Val Ser Leu Trp Gln Gly Glu Thr Gln Val Ala Ser Gly
225                 230                 235                 240

Thr Ala Pro Phe Gly Gly Glu Ile Ile Asp Glu Arg Gly Gly Tyr Ala
                245                 250                 255

Asp Arg Val Thr Leu Arg Leu Asn Val Glu Asn Pro Lys Leu Trp Ser
            260                 265                 270

Ala Glu Ile Pro Asn Leu Tyr Arg Ala Val Val Glu Leu His Thr Ala
```

```
                275                 280                 285
Asp Gly Thr Leu Ile Glu Ala Glu Ala Cys Asp Val Gly Phe Arg Glu
                    290                 295                 300
Val Arg Ile Glu Asn Gly Leu Leu Leu Asn Gly Lys Pro Leu Leu
305                 310                 315                 320
Ile Arg Gly Val Asn Arg His Glu His His Pro Leu His Gly Gln Val
                    325                 330                 335
Met Asp Glu Gln Thr Met Val Gln Asp Ile Leu Leu Met Lys Gln Asn
                340                 345                 350
Asn Phe Asn Ala Val Arg Cys Ser His Tyr Pro Asn His Pro Leu Trp
                355                 360                 365
Tyr Thr Leu Cys Asp Arg Tyr Gly Leu Tyr Val Val Asp Glu Ala Asn
            370                 375                 380
Ile Glu Thr His Gly Met Val Pro Met Asn Arg Leu Thr Asp Asp Pro
385                 390                 395                 400
Arg Trp Leu Pro Ala Met Ser Glu Arg Val Thr Arg Met Val Gln Arg
                405                 410                 415
Asp Arg Asn His Pro Ser Val Ile Ile Trp Ser Leu Gly Asn Glu Ser
                420                 425                 430
Gly His Gly Ala Asn His Asp Ala Leu Tyr Arg Trp Ile Lys Ser Val
                435                 440                 445
Asp Pro Ser Arg Pro Val Gln Tyr Glu Gly Gly Gly Ala Asp Thr Thr
            450                 455                 460
Ala Thr Asp Ile Ile Cys Pro Met Tyr Ala Arg Val Asp Glu Asp Gln
465                 470                 475                 480
Pro Phe Pro Ala Val Pro Lys Trp Ser Ile Lys Lys Trp Leu Ser Leu
                485                 490                 495
Pro Gly Glu Thr Arg Pro Leu Ile Leu Cys Glu Tyr Ala His Ala Met
                500                 505                 510
Gly Asn Ser Leu Gly Gly Phe Ala Lys Tyr Trp Gln Ala Phe Arg Gln
                515                 520                 525
Tyr Pro Arg Leu Gln Gly Gly Phe Val Trp Asp Trp Val Asp Gln Ser
                530                 535                 540
Leu Ile Lys Tyr Asp Glu Asn Gly Asn Pro Trp Ser Ala Tyr Gly Gly
545                 550                 555                 560
Asp Phe Gly Asp Thr Pro Asn Asp Arg Gln Phe Cys Met Asn Gly Leu
                    565                 570                 575
Val Phe Ala Asp Arg Thr Pro His Pro Ala Leu Thr Glu Ala Lys His
                580                 585                 590
Gln Gln Gln Phe Phe Gln Phe Arg Leu Ser Gly Gln Thr Ile Glu Val
                595                 600                 605
Thr Ser Glu Tyr Leu Phe Arg His Ser Asp Asn Glu Leu Leu His Trp
610                 615                 620
Met Val Ala Leu Asp Gly Lys Pro Leu Ala Ser Gly Glu Val Pro Leu
625                 630                 635                 640
Asp Val Ala Pro Gln Gly Lys Gln Leu Ile Glu Leu Pro Glu Leu Pro
                645                 650                 655
Gln Pro Glu Ser Ala Gly Gln Leu Trp Leu Thr Val Arg Val Val Gln
                660                 665                 670
Pro Asn Ala Thr Ala Trp Ser Glu Ala Gly His Ile Ser Ala Trp Gln
                675                 680                 685
Gln Trp Arg Leu Ala Glu Asn Leu Ser Val Thr Leu Pro Ala Ala Ser
            690                 695                 700
```

His Ala Ile Pro His Leu Thr Thr Ser Glu Met Asp Phe Cys Ile Glu
705                 710                 715                 720

Leu Gly Asn Lys Arg Trp Gln Phe Asn Arg Gln Ser Gly Phe Leu Ser
            725                 730                 735

Gln Met Trp Ile Gly Asp Lys Lys Gln Leu Leu Thr Pro Leu Arg Asp
        740                 745                 750

Gln Phe Thr Arg Ala Pro Leu Asp Asn Asp Ile Gly Val Ser Glu Ala
        755                 760                 765

Thr Arg Ile Asp Pro Asn Ala Trp Val Glu Arg Trp Lys Ala Ala Gly
770                 775                 780

His Tyr Gln Ala Glu Ala Leu Leu Gln Cys Thr Ala Asp Thr Leu
785                 790                 795                 800

Ala Asp Ala Val Leu Ile Thr Thr Ala His Ala Trp Gln His Gln Gly
                805                 810                 815

Lys Thr Leu Phe Ile Ser Arg Lys Thr Tyr Arg Ile Asp Gly Ser Gly
                820                 825                 830

Gln Met Ala Ile Thr Val Asp Val Glu Val Ala Ser Asp Thr Pro His
        835                 840                 845

Pro Ala Arg Ile Gly Leu Asn Cys Gln Leu Ala Gln Val Ala Glu Arg
850                 855                 860

Val Asn Trp Leu Gly Leu Gly Pro Gln Glu Asn Tyr Pro Asp Arg Leu
865                 870                 875                 880

Thr Ala Ala Cys Phe Asp Arg Trp Asp Leu Pro Leu Ser Asp Met Tyr
                885                 890                 895

Thr Pro Tyr Val Phe Pro Ser Glu Asn Gly Leu Arg Cys Gly Thr Arg
                900                 905                 910

Glu Leu Asn Tyr Gly Pro His Gln Trp Arg Gly Asp Phe Gln Phe Asn
        915                 920                 925

Ile Ser Arg Tyr Ser Gln Gln Gln Leu Met Glu Thr Ser His Arg His
930                 935                 940

Leu Leu His Ala Glu Glu Gly Thr Trp Leu Asn Ile Asp Gly Phe His
945                 950                 955                 960

Met Gly Ile Gly Gly Asp Asp Ser Trp Ser Pro Ser Val Ser Ala Glu
                965                 970                 975

Phe Gln Leu Ser Ala Gly Arg Tyr His Tyr Gln Leu Val Trp Cys Gln
        980                 985                 990

Lys

<210> SEQ ID NO 7
<211> LENGTH: 34
<212> TYPE: DNA
<213> ORGANISM: Artificial Sequence
<220> FEATURE:
<223> OTHER INFORMATION: synthetic sequence

<400> SEQUENCE: 7
atcgacggat ccatgcagaa acaacctaca tggg                          34

<210> SEQ ID NO 8
<211> LENGTH: 31
<212> TYPE: DNA
<213> ORGANISM: Artificial Sequence
<220> FEATURE:
<223> OTHER INFORMATION: synthetic sequence

<400> SEQUENCE: 8
ctgagtcaat gtttatttat agtctcatag c                             31

DETECTION OF SUB-CELLULAR COMPARTMENT LOCALIZATION OF A MOLECULE USING A REDUCED AFFINITY ENZYME COMPLEMENTATION REPORTER SYSTEM

CROSS-REFERENCE TO RELATED APPLICATIONS

This application claims the benefit under 35 U.S.C. §119 (e) of prior U.S. provisional application Ser. No. 60/877,260 filed Dec. 26, 2006, disclosures of which applications are herein incorporated by reference.

GOVERNMENT RIGHTS

This invention was made with government support under federal grant nos. T32 GM08412; T32 AG0259; AF051678; HD018179; AG009521; AG024987; AG020961; DAMD17-00-1-0442 awarded by the National Institutes of Health. The United States Government has certain rights in this invention.

INTRODUCTION

The localization/translocation of molecules to distinct sub-cellular compartments within a cell is important for a number of cellular processes, including the regulation of cell-surface receptor expression and signaling as well as the uptake of extracellular molecules. As such, detecting the sub-cellular localization of specific molecules, as well as their translocation to and from distinct intracellular compartments, is an important step toward understanding the role they play in biological systems. Furthermore, the development of therapies for the treatment of a number of human diseases as well as regulation of immune responses depends upon an understanding of the sub-cellular location and translocation of specific molecules.

As such, systems for detecting the sub-cellular localization and translocation of molecules to and from specific sub-cellular compartments find wide application in a variety of different applications.

SUMMARY

Methods and compositions for detecting the sub-cellular localization of a molecule are provided. Aspects of the invention include a method of detecting translocation of a cell-surface receptor to a sub-cellular compartment, the method including the steps of:
(a) providing a cell including: (i) a first fusion protein including a cell-surface receptor and a first β-galactosidase fragment; and (ii) a second fusion protein including a protein that localizes to a sub-cellular compartment and a second β-galactosidase fragment; wherein the first and second β-galactosidase fragments complement one another to produce an active β-galactosidase enzyme when in close proximity, and at least one of the β-galactosidase fragments is altered such that the first and second β-galactosidase fragments have a reduced affinity for each other as compared to wild type fragments; and
(b) evaluating the cell for active β-galactosidase activity to detect translocation of the cell-surface receptor to the sub-cellular compartment.

In certain embodiments, the providing step includes introducing nucleic acids encoding the first and second fusion proteins into the cell.

In certain embodiments, the method further includes contacting the cell with an agent prior to the evaluating.

In certain embodiments, the agent is selected from one or more of: ligand for the cell-surface receptor, antagonist of the cell-surface receptor, test compound, candidate therapeutic agent, candidate ligand or agonist of the cell-surface receptor, candidate antagonist of the cell-surface receptor.

In certain embodiments, the method further includes evaluating β-galactosidase activity before and after the contacting.

In certain embodiments, the cell surface receptor is a G protein coupled receptor (GPCR).

In certain embodiments, the cell surface receptor is selected from the group consisting of: cytokine receptor, chemokine receptor, and antigen receptor.

In certain embodiments, the cell is a mammalian cell.

In certain embodiments, the cell is a yeast cell.

In certain embodiments, the sub-cellular compartment is the endosome.

In certain embodiments, the protein that localizes to the sub-cellular compartment includes an endofin FYVE domain.

In certain embodiments, the first β-galactosidase fragment is a variant minimal N-terminal β-galactosidase peptide.

In certain embodiments, the variant minimal N-terminal β-galactosidase peptide includes at least one amino acid variation as compared to a β-galactosidase fragment consisting of amino acids 3 to 92 of *E. coli* wild-type β-galactosidase.

In certain embodiments, the second β-galactosidase fragment is a deletion mutant of the wild type *E. coli* β-galactosidase protein.

In certain embodiments, the deletion mutant is selected from: the M15 acceptor fragment and the M112 dimer.

In certain embodiments, the evaluating step occurs in vivo.

Aspects of the present invention include a cell that includes:
(a) a first fusion protein including a cell-surface receptor and a first β-galactosidase fragment; and
(b) a second fusion protein including a protein that localizes to a sub-cellular compartment and a second β-galactosidase fragment; wherein the first and second β-galactosidase fragments complement one another to produce an active β-galactosidase enzyme when in close proximity, and at least one of the β-galactosidase fragments is altered such that the first and second β-galactosidase fragments have a reduced affinity for each other as compared to wild type fragments.

Aspects of the present invention include a kit that contains:
(a) cell including: (i) a first fusion protein including a cell-surface receptor and a first β-galactosidase fragment; and (ii) a second fusion protein including a protein that localizes to a sub-cellular compartment and a second β-galactosidase fragment; wherein the first and second β-galactosidase fragments complement one another to produce an active β-galactosidase enzyme when in close proximity, and at least one of the β-galactosidase fragments is altered such that the first and second β-galactosidase fragments have a reduced affinity for each other as compared to wild type fragments; and
(b) a β-galactosidase substrate.

Aspects of the present invention include a kit that contains:
(a) a first expression vector encoding a first β-galactosidase fragment, wherein the first expression vector includes a restriction site positioned such that when a protein coding sequence is inserted into the vector using the restriction site, the vector encodes a fusion protein of the protein and a β-galactosidase fragment; and
(b) a second expression vector encoding a fusion protein including a protein that localizes to a sub-cellular compartment and a second β-galactosidase fragment; wherein the first and second β-galactosidase fragments complement one another to produce an active β-galactosidase enzyme when in close proximity, and at least one of the β-galactosidase fragments is altered such that the first and second β-galactosidase fragments have a reduced affinity for each other as compared to wild type fragments.

In certain embodiments, the kit further includes one or more of:
  (i) a host cell capable of expressing proteins encoded in the first and second expression vectors;
  (ii) a β-galactosidase substrate; and
  (iii) instructions for practicing the subject methods.

DEFINITIONS

Figure 1:
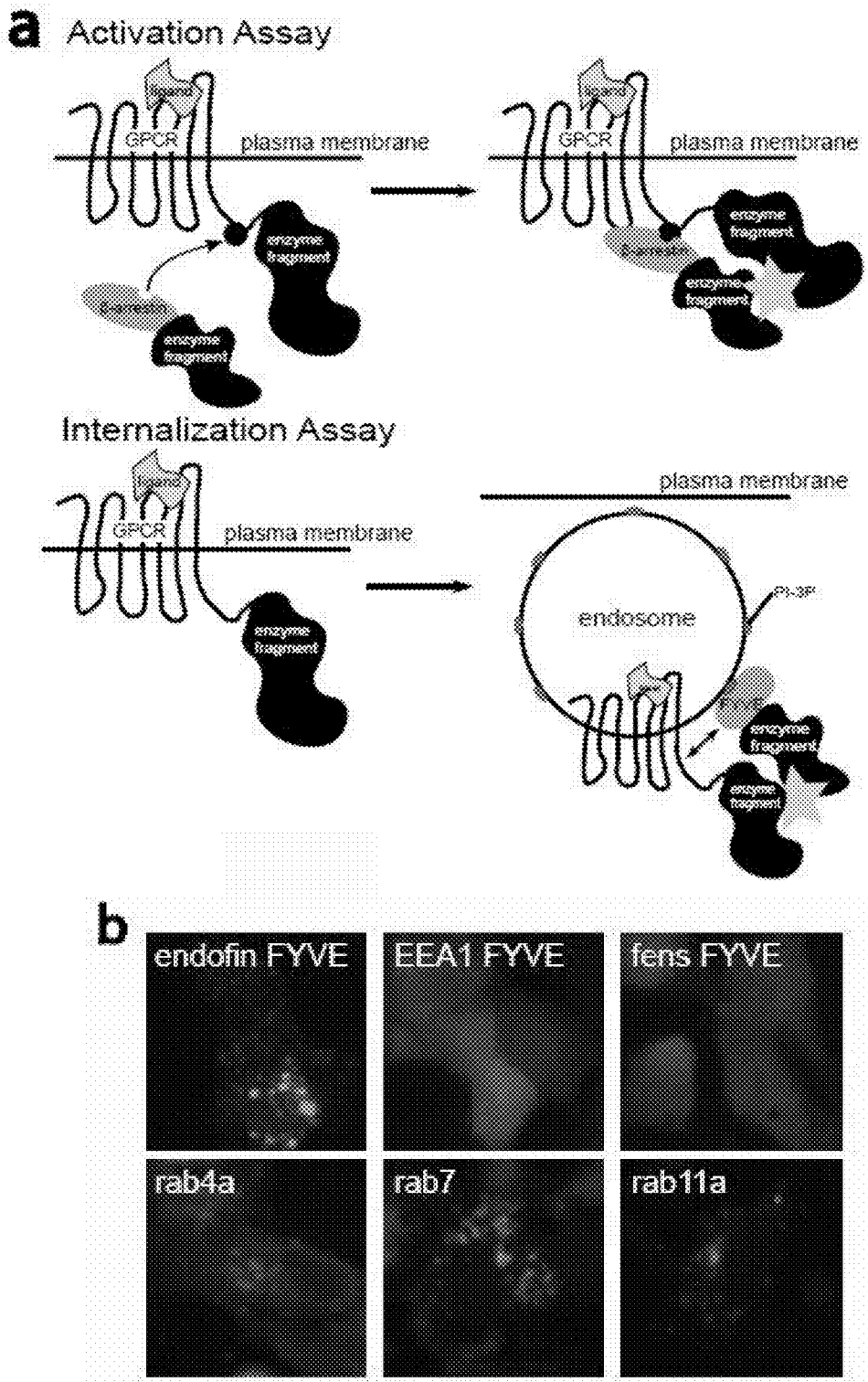
FIG. 1. (a) β-galactosidase complementation assay schemes. Top scheme shows the internalization assay, where the receptor (GPCR) is coupled to the ω fragment and the FYVE domain of endofin is coupled to the α fragment; upon internalization, the receptor colocalizes with PI-3P-positive endosomes coated with FYVE domains. Bottom scheme shows the activation assay, where the receptor is coupled to the α fragment and β-arrestin to the ω fragment; upon ligand binding, β-arrestin is recruited to the receptor, reconstituting β-galactosidase. "Enzyme fragment" refers to either ω or eYFP-α. (b) Localization of various protein-YFP-α peptide fusions; endofin FYVE, EEA1 FYVE, and fens FYVE refer to the isolated FYVE domains of the respective protein. Notice that, of the FYVE domains, only that of endofin was sufficient to cause endosomal localization. (c) Timecourse of β2-adrenergic receptor stimulation with 10 μM isoproterenol: top panel shows internalization assay as in (a), while bottom panel shows fluorescence of β2AR-eYFP-α; note the punctuate appearance of internalized β2AR. (d) Dose response of β2-adrenergic receptor in the internalization assay (FYVE-ω+GPCR-eYFP-α, open circles) and activation assay (β-arrestin-ω+GPCR-eYFP-α, filled circles) at 1 h. Also shown are the best-fit sigmoidal dose-response curves. Error bars represent standard deviations of 2-4 biological replicates.
Figure 1:
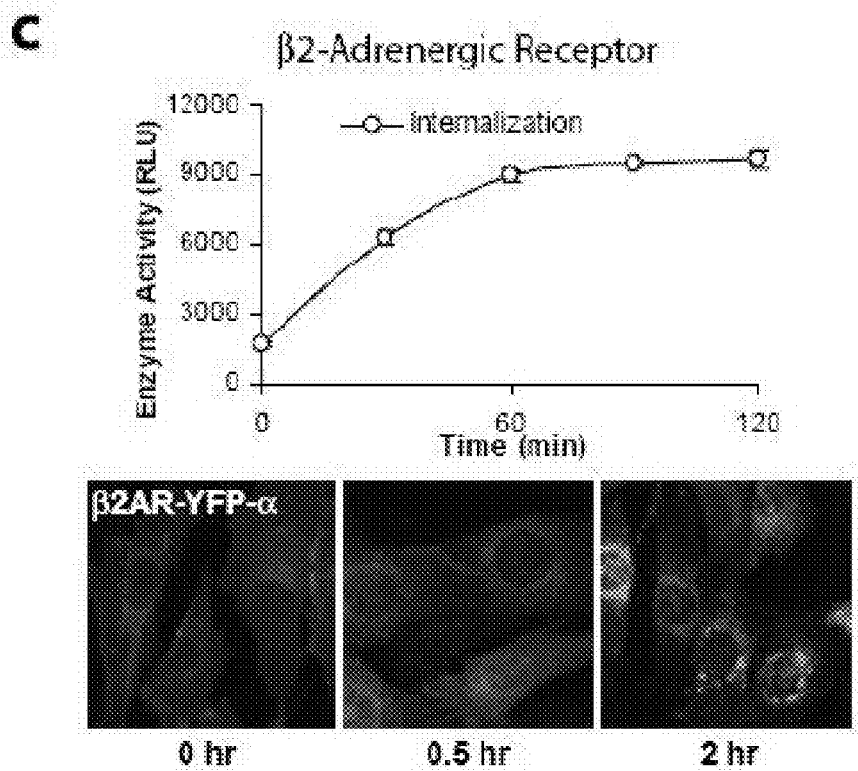
Figure 1:
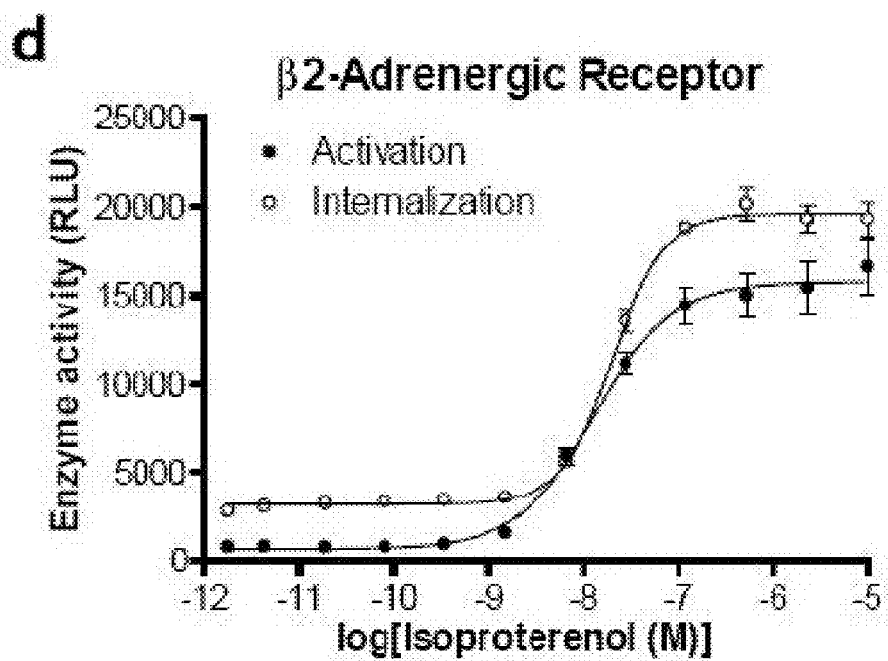

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "peptide" as used herein refers to any polymer compound produced by amide formation between an α-carboxyl group of one amino acid and an α-amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "fusion protein" as used herein is a protein created through genetic engineering from two or more proteins/peptides. In general, this is achieved by creating a "fusion gene", a nucleic acid that encodes the fusion protein. For example, a fusion gene that encodes a fusion protein may be made by removing the stop codon from a first DNA sequence encoding the first protein, then appending a DNA sequence encoding the second protein in frame. The resulting fusion gene sequence will then be expressed by a cell as a single fusion protein. Fusion proteins may include a linker (or "spacer") sequence which can promote appropriate folding and activity of each domain of the fusion protein. Fusion proteins may also include epitope tags for identification (e.g., in western blots, immunofluorescence, etc.) and/or purification. Non-limiting examples of epitope tags in current use include: HA, myc, FLAG, and 6-HIS.

As used herein, the term "amino acid" is intended to include not only the L, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243 (1969), 3552-59 is used.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides. As such, a "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

The term "oligonucleotide" as used herein denotes single-stranded nucleotide multimers of from about 10 to about 100 nucleotides and up to 200 nucleotides in length.

The term "polynucleotide" as used herein refers to single- or double-stranded polymers composed of nucleotide monomers of generally greater than about 100 nucleotides in length.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

A "vector" is a replicon, such as plasmid, phage or cosmid, to which another DNA segment may be attached so as to bring about the replication of the attached segment.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

"Optional" or "optionally" means that the subsequently described circumstance may or may not occur so that the description includes instances where the circumstance occurs and instances where it does not.

"Contacting" means to bring or put together. As such, a first item is contacted with a second item when the two items are brought or put together, e.g., by touching them to each other.

The term "agonist" as used herein refers to a molecule or substance that binds to or otherwise interacts with a receptor or enzyme to increase activity of that receptor or enzyme. Agonist as used herein encompasses both full agonists and partial agonists.

The term "antagonist" as used herein refers to a molecule that binds to or otherwise interacts with a receptor to block (e.g., inhibit) the activation of that receptor or enzyme by an agonist.

The term "ligand" as used herein refers to a naturally occurring or synthetic compound that binds to a protein receptor. Upon binding to a receptor, ligands generally lead to the modulation of activity of the receptor. The term is intended to encompass naturally occurring compounds, synthetic compounds and/or recombinantly produced compounds. As used herein, this term can encompass agonists, antagonists, and inverse agonists.

The term "receptor" as used herein refers to a protein normally found on the surface of a cell which, when activated, leads to a signaling cascade in a cell.

The term "functional interaction" as used herein refers to an interaction between a receptor and ligand that results in modulation of a cellular response. These may include changes in membrane potential, secretion, action potential generation, activation of enzymatic pathways and long term structural changes in cellular architecture or function.

The term "sub-cellular compartment localized" as used herein refers to a molecule (e.g., a peptide, protein, etc.) that, when present in a cell, is found predominantly associated with a specific sub-cellular compartment. Sub-cellular compartments of interest include, but are not limited to, lysosomes, endosomes, the Golgi apparatus, the endoplasmic reticulum, the nucleus, chloroplasts and mitochondria. A sub-cellular compartment localized molecule may be naturally occurring or one that has been engineered (e.g., genetically engineered) to predominantly associate with the sub-cellular compartment of interest.

The terms "G protein coupled receptors" and "GPCRs" as used interchangeably herein include all subtypes of the opioid, muscarinic, dopamine, adrenergic, adenosine, rhodopsin, angiotensin, serotonin, thyrotropin, gonadotropin, substance K, substance P and substance R receptors, melanocortin, metabotropic glutamate, or any other GPCR known to couple via G proteins. This term also includes orphan receptors that are known to couple to G proteins, but for which no specific ligand is known.

DETAILED DESCRIPTION

Methods and compositions for determining the sub-cellular localization of a molecule in cells are provided. Aspects of the invention include the use of a reduced affinity enzyme complementation reporter system, such as a reduced affinity β-galactosidase complementation reporter system. Also provided are systems and kits for use in practicing embodiments of the methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, aspects of the methods are reviewed first in greater detail, followed by a review of different applications in which embodiments of the methods find use, as well as a review of various kits that find use in practicing certain embodiments of the invention.

Methods

As summarized above, embodiments of the invention provide methods of determining the sub-cellular localization of one or more molecules in a cell. As such, embodiments of the invention provide methods of determining whether a molecule of interest is co-localized with a sub-cellular compartment localized molecule. Molecules of interest include a variety of different types, where in certain embodiments the molecule of interest is a polypeptide (e.g., protein).

As summarized above, embodiments of the invention are directed to methods of determining the sub-cellular localization of a molecule (e.g., a protein) in cells. The methods include providing a cell having: 1) a first molecule (i.e., the molecule of interest) labeled with a first member of a reduced-affinity enzyme complementation reporter system, and 2) a second sub-cellular compartment localized molecule labeled with a second member of the reduced-affinity enzyme complementation system. The cell is then evaluated for activity of the reporter enzyme, and the result of the evaluation is employed to determine whether the first molecule is associated with the same sub-cellular compartment as the second molecule. In general, higher levels of detected enzyme activity indicate increased amounts of the first molecule co-localized with the second sub-cellular compartment localized molecule. In addition, the low affinity reporter subunits, when co-localized to the same sub-cellular compartment by virtue of their attached molecules, should not be physically or spatially prevented from complementation. For example, if co-localization to the endosomal membrane is being assayed, the low-affinity reporter subunits, when co-localized, should be present on the same side of the endosomal membrane.

Aspects of the methods include the use of a reduced-affinity enzyme complementation reporter system. By "reduced-affinity" enzyme complementation reporter system is meant a system that is made up of two or more fragments of an enzyme (i.e., reporter subunits) that by themselves lack any of the detectable activity (which may be directly or indirectly detectable) that is observed in their parent enzyme but when brought sufficiently close together, e.g., through random interaction or a binding interaction mediated through their respective attached molecules, give rise to a detectable amount of the activity of the parent enzyme. An aspect of the reduced affinity enzyme complementation reporter systems of the invention is that at least one of the reporter subunits employed in the system is a variant of a corresponding domain in its wild-type parent enzyme such that its interaction with the other subunit(s) of the system is reversible under assay conditions, absent a binding interaction mediated through their respective attached molecules. As such, the reduced-affinity enzyme complementation reporter systems of the present invention provide for a first detectable signal when the enzyme subunits are not associated with the same sub-cellular compartment (e.g., present in or on separate sub-cellular compartments) that is less than a second detectable signal that is observed when the enzyme subunits are associated with the same-sub-cellular compartment (e.g., within or on the outer membrane of an endosome). In certain embodiments, the enzyme subunits employed in the system are derived from a β-galactosidase enzyme (as reviewed in greater detail below). In addition, aspects of the invention include embodiments where the magnitude of the first signal under a given set of assay conditions of interest is known, and may be determined at the time the second signal is detected or at some previous time, where the value of the previous detection is used as a reference. Embodiments of the reduced-affinity enzyme complementation reporter systems are characterized by providing high signal-to-noise ratios. In certain embodiments, the signal-to-noise ratio observed in the reporter system is from about 3 to about 100, from about 3 to about 50, and including from about 3 to about 10.

Reporter subunits which have sufficiently low binding affinity such that they exhibit reversible binding to each other and yet are still capable of associating and generating a detectable signal upon co-localization within or on a sub-cellular compartment (e.g., endosome), can be produced using a number of different approaches. In certain embodiments, a rational approach is employed in which a first reporter system that is made up of high affinity subunits is studied to identify those regions of the subunits that are responsible for the high affinity association of the subunits. The identified region(s) is then varied in some way, e.g., by introducing point mutations, insertions or deletions into the region, to obtain a suitable low affinity subunit and thereby obtain a reduced affinity reporter system in which the subunits reversibly interact in the absence of any binding member mediated association. See e.g., the experimental section below, as well as U.S. patent application Ser. No. 11/132,764 filed on May 18, 2005 for a review of such a rational approach as employed with an initial high affinity β-galactosidase complementation reporter system (incorporated herein by reference). Reporter subunits which can be used include any reduced binding affinity subunits which are capable of associating to produce a detectable signal. In one embodiment, the reporter subunits are proteins which are capable of associating and are capable, when associated, of catalyzing a reaction which produces a directly or indirectly detectable product from a cognate substrate.

Reduced affinity enzyme complementation reporter systems that are used in certain embodiments of the invention can employ reporter subunits derived from a number of different enzymes. Enzymes of interest from which reporter subunits may be derived include, but are not limited to: β-galactosidase, β-glucuronidase (GUS), β-lactamase, alkaline phosphatase, peroxidase, chloramphenicol acetyltransferase (CAT), cre-recombinase and luciferase.

In certain embodiments, the enzyme upon which the reduced-affinity enzyme complementation reporter system is based is wild-type $E.\ coli$ β-galactosidase, which is encoded by the $E.\ coli$ lacZ gene. β-galactosidase activity may be measured by a range of methods including live-cell flow cytometry and histochemical staining with the chromogenic substrate 5-bromo-4-chloro-3-indolyl β-D-galactopyranoside (X-Gal). See e.g., Nolan et al., Proc. Natl. Acad. Sci., USA, 85:2603-2607 (1988); and Lojda, Z., Enzyme Histochemistry: A Laboratory Manual, Springer, Berlin, (1979).

For illustrative purposes only, the invention is now further described primarily in terms of embodiments in which the reduced affinity enzyme complementation reporter system is a β-galactosidase enzyme complementation reporter system, i.e., where the reporter subunits are β-galactosidase fragments, where the fragments may have amino acid sequences found in their corresponding wild-type β-galactosidase molecules or have sequences that are variants of sequences found in their corresponding wild-type β-galactosidase molecules.

In certain embodiments, the employed reduced affinity β-galactosidase complementation reporter system is one that is made up of two or more β-galactosidase fragments or variants thereof. For example, in certain embodiments, the reporter system includes a first and second fragment of β-galactosidase (e.g., an α and ω fragment). In yet other embodiments, the reporter system may include more than two β-galactosidase fragments, such as a first, second and third β-galactosidase fragments (e.g., an α, μ and ω fragment).

In certain embodiments, the reduced-affinity β-galactosidase complementation signal producing system employed in embodiments of the subject methods is one that is made up of first and second fragments of β-galactosidase (i.e., first and second β-galactosidase fragments), where the first and second fragments have an affinity for each other that provides for different levels of β-galactosidase activity depending on whether the sub-cellular compartment co-localization of interest has occurred. As such, the first and second β-galactosidase fragments have an affinity for each other that provides a known first level of β-galactosidase activity in the absence of sub-cellular compartment co-localization and a second, different level of β-galactosidase activity when sub-cellular compartment co-localization of the fragments occurs. In this manner, by determining the activity level of the signal producing system, a determination can be made as to whether the molecule of interest is associated with (e.g., present within or on) the same sub-cellular compartment as the sub-cellular compartment localized molecule.

The first and second β-galactosidase fragments are ones that have a low affinity for each other, where the low affinity is sufficient to provide for differing interaction dependent activity levels reviewed above. As the fragments of the signal producing system have a low affinity for each other, the activity level (as determined using the assay reported in the Experimental Section below) that is observed from the system made up of the fragments in the absence of a polypeptide interaction of interest is less than the activity level that is observed in the absence of an interaction of interest with the β-galactosidase complementation system reported in Langley et al., Proc. Nat'l Acad. Sci. USA (1975) 72: 1254-1257.

Aspects of these embodiments include the use of a first β-galactosidase fragment (also known as an enzyme donor or α fragment) that is a variant minimal N-terminal β-galactosidase peptide. By minimal N-terminal β-galactosidase peptide is meant that the peptide has an amino acid sequence that is found in the N-terminal region of a wild-type β-galactosidase protein, e.g., a sequence that starts within about 10 residues of the N-terminus, such as within about 5 residues of the N-terminus of a wild-type β-galactosidase protein. As the first β-galactosidase fragments of this embodiment are minimal, they are, in certain embodiments, about 60 amino acids or less in length, such as about 55 amino acids in length or less, including about 50 amino acids or less in length, e.g., 49 amino acids or less in length, 48 amino acids or less in length, etc.

As the minimal N-terminal β-galactosidase peptides are variants, they include at least one sequence variation as compared to the corresponding sequence in the N-terminal domain of the corresponding wild-type β-galactosidase protein. The sequence variation may be an insertion, deletion or substitution, e.g., in the form of a point mutation. The variant may have a single variation (e.g., insertion, deletion, point mutations) or two or more different variations, such as two or more point mutations, etc. In certain embodiments, the first β-galactosidase fragment has a binding affinity for the second β-galactosidase fragment (described in greater detail below) which is less than the binding affinity of a fragment having the complete sequence from amino acid residue 3 to 92 (e.g., as described in Langley et al., J. Biol. Chem. (1975) 250:2587-2592) of wild-type E. coli β-galactosidase for the second β-galactosidase fragment, e.g., where the binding affinity is less than the wild-type fragment for the second β-galactosidase fragment.

In certain embodiments, any variation in sequence occurs in a region of the β-galactosidase fragment that, upon complementation of the fragment with the second fragment of the system, is in a "buried" location within the second β-galactosidase fragment. In certain embodiments, this domain includes the sequence found from amino acid residue 29 to 41 of the wild-type sequence, and therefore the fragment includes a variation in this region, e.g., from amino acid residue 29 to 41, such as from amino acid residue 31 to 41. For example, where the variations are point mutations, the variant may include one or more point mutations at any of amino acid residues 29 to 41, such that one or more of these 13 amino acid residues may be substituted, including 2 or more, three or more, four or more etc., of these amino acid residues may be substituted. Specific amino acid point mutations of interest include, but are not limited to: H31 (e.g., H31R); F34 (e.g., F34Y); E41 (e.g., E41Q); and N39 (e.g., N39Q, N39D).

Exemplary α peptide sequences include:

```
                                            SEQ ID NO: 1
(H31R)
MGVITDSLAVVLQRRDWENPGVTQLNRLAARPPFASWRNSEEARTDRPSQ

QL

SEQ ID NO: 2
(F34Y)
MGVITDSLAVVLQRRDWENPGVTQLNRCAAHPPYASWRNSEEARTDRPSQ

QL

SEQ ID NO: 3
(E41Q)
MGVITDSLAVVLQRRDWENPGVTQLNRLAAHPPFASWRNSQEARTDRPSQ

QL

SEQ ID NO: 4
(N39D)
MGVITDSLAVVLQRRDWENPGVTQLNRLAAHPPFASWRDSEEARTDRPSQ

QL

SEQ ID NO: 5
(Truncated)
MGVITDSLAVVLQRRDWENPGVTQLNRLAAHPPFASWRDSEEA
```

In embodiments where the first fragment is a variant minimal N-terminal β-galactosidase fragment, as reviewed above, the first fragment may be used in conjunction with one or more additional fragments, as reviewed above. In certain embodiments as reviewed above, the reporter system is made up of a first and a second β-galactosidase fragment. The second β-galactosidase fragment may be any fragment that is capable of interacting with the first β-galactosidase fragment to provide for detectable β-galactosidase activity. The second β-galactosidase fragment may include a major portion of the β-galactosidase enzyme, corresponding to greater than about 60%, greater than about 80%, or greater than about 90% of the full-length β-galactosidase enzyme, based on molecular weight of the full-length β-galactosidase enzyme. In certain embodiments, the second β-galactosidase fragment is a deletion mutant that is missing aa 11-41 of the wild type E. coli β-galactosidase protein (e.g., as described in Langley et al., Proc. Nat'l Acad. Sci. USA (1975) 72: 1254-1257), which fragment is known as the M15 acceptor or ω fragment. Other specific acceptors (i.e., ω-fragments) of interest include, but are not limited to: the M112 dimer, a deletion of amino acids 23-31 within β-galactosidase (Lin, Villarejo and Zabin, 1970, Biochem. Biophys. Res. Common. 40:249; Celeda and Zabin, 1979, Biochem. 18:404; Welphy, Fowler and Zabin, 1981, J. Biol. Chem. 256:6804; Langley et al., 1975, Proc. Natl. Acad. Sci. USA 72:1254). One exemplary ω peptide sequence is set forth as SEQ ID NO:6:

```
MGVITDSLAVVARTDRPSQQLRSLNGEWRFAWFPAPEAVPESWLECDLPE

ADTVVVPSNWQMHGYDAPIYTNVTYPITVNPPFVPTENPTGCYSLTFNVD

ESWLQEGQTRIIFDGVNSAFHLWCNGRWVGYGQDSRLPSEFDLSAFLRAG

ENRLAVMVLRWSDGSYLEDQDMWRMSGIFRDVSLLHKPTTQISDFHVATR

FNDDFSRAVLEAEVQMCGELRDYLRVTVSLWQGETQVASGTAPFGGEIID

ERGGYADRVTLRLNVENPKLWSAEIPNLYRAVVELHTADGTLIEAEACDV

GFREVRIENGLLLLNGKPLLIRGVNRHEHHPLHGQVMDEQTMVQDILLMK

QNNFNAVRCSHYPNHPLWYTLCDRYGLYVVDEANIETHGMVPMNRLTDDP

RWLPAMSERVTRMVQRDRNHPSVIIWSLGNESGHGANHDALYRWIKSVDP

SRPVQYEGGGADTTATDIICPMYARVDEDQPFPAVPKWSIKKWLSLPGET

RPLILCEYAHAMGNSLGGFAKYWQAFRQYPRLQGGFVWDWVDQSLIKYDE

NGNPWSAYGGDFGDTPNDRQFCMNGLVFADRTPHPALTEAKHQQQFFQFR

LSGQTIEVTSEYLFRHSDNELLHWMVALDGKPLASGEVPLDVAPQGKQLI

ELPELPQPESAGQLWLTVRVVQPNATAWSEAGHISAWQQWRLAENLSVTL

PAASHAIPHLTTSEMDFCIELGNKRWQFNRQSGFLSQMWIGDKKQLLTPL

RDQFTRAPLDNDIGVSEATRIDPNAWVERWKAAGHYQAEAALLQCTADTL

ADAVLITTAHAWQHQGKTLFISRKTYRIDGSGQMAITVDVEVASDTPHPA

RIGLNCQLAQVAERVNWLGLGPQENYPDRLTAACFDRWDLPLSDMYTPYV

FPSENGLRCGTRELNYGPHQWRGDFQFNISRYSQQQLMETSHRHLLHAEE

GTWLNIDGFHMGIGGDDSWSPSVSAEFQLSAGRYHYQLVWCQK.
```

Aspects of the invention include the use of the reduced-affinity reporter systems described above to detect sub-cellular compartment localization of molecules of interest, e.g., co-localization of a molecule of interest and a sub-cellular compartment localized protein. In certain embodiments a cell is provided that includes the molecule of interest (e.g., a protein) and the sub-cellular compartment localized protein stably associated with a different member of the reporter system. For example, where the system is employed to detect the co-localization of a first and second sub-cellular compartment localized protein, a cell is provided that includes the first protein stably associated with a first reporter subunit, e.g., the variant minimal N-terminal β-galactosidase fragment described above, while the second sub-cellular compartment localized protein is stably associated with a second reporter subunit, e.g., the M15 ω fragment described above.

By "stably associated" is meant that the reporter subunit and the molecular entity are bound to each other, either covalently or otherwise, e.g., via a sufficiently high affinity interaction, such that they do not disassociate from each other under the assay conditions in which they are employed, as further illustrated below.

The moieties (or molecules) assayed for sub-cellular compartment localization employing the methods of the subject invention are those that can be stably associated with (i.e., attached to) one of the reporter subunits. Moieties of interest can be any of a range of different molecules including carbohydrates, lipids, proteins, and nucleic acids, as well as portions, polymers and analogues thereof, provided they are capable of being linked to the reporter subunit (e.g., in the form of a fusion protein). In certain embodiments, the moieties of interest are plasma membrane moieties (e.g., cell surface receptors) or moieties that stably associate with plasma membrane moieties (e.g., ligands for cell surface receptors, co-receptors, membrane component binding molecules, etc), such that the sub-cellular co-localization event that is detected is one that occurs between the plasma-membrane and another sub-cellular compartment (e.g., the endosomal trafficking of a cell surface receptor).

Exemplary proteins that can be monitored for sub-cellular compartment localization include members of a signal transduction cascade, proteins regulating apoptosis, proteins that regulate progression of the cell-cycle or development of tumors, transcriptional regulatory proteins, translational regulatory proteins, proteins that affect cell interactions, cell adhesion molecules (CAMs), ligand-receptor pairs, proteins that participate in the folding of other proteins, and proteins involved in targeting to particular intracellular compartments, such as the Golgi apparatus, endoplasmic reticulum, ribosomes, chloroplasts and mitochondria. Other exemplary proteins include protein hormones and cytokines. Cytokines include those involved in signal transduction, such as interferons, chemokines, and hematopoietic growth factors. Other exemplary proteins include interleukins, lymphotoxin, transforming growth factors-α and β, macrophage and granulocyte colony stimulating factors, soluble antigens and peptides. Other proteins include intracellular enzymes such as protein kinases, phosphatases and synthases. Exemplary proteins involved in apoptosis include tumor necrosis factor (TNF), Fas ligand, interleukin-1βconverting enzyme (ICE) proteases, and TNF-related apoptosis-inducing ligand (TRAIL). Proteins involved in the cell cycle include deoxyribonucleic acid (DNA) polymerases, proliferating cell nuclear antigen, telomerase, cyclins, cyclin dependent kinases, tumor suppressors and phosphatases. Proteins involved in transcription and translation include ribonucleic acid (RNA) polymerases, transcription factors, enhancer-binding proteins and ribosomal proteins. Proteins involved in cellular interactions such as cell-to-cell signaling include receptor proteins, and peptide hormones or their enhancing or inhibitory mimics.

In certain embodiments, the molecules of interest whose sub-cellular localization can be determined by the subject invention are cell surface receptors. Exemplary cell surface receptor families include G-protein coupled receptors, cytokine receptors, chemokine receptors, antigen receptors (e.g., cell surface-expressed antibodies and T cell receptors). In certain of these embodiments, the internalization and trafficking of a cell surface receptor to the endosomal compartment is determined using the systems and methods of the present invention. In certain embodiments, the molecule of interest and the sub-cellular compartment localized molecule are associated to one another, either directly or indirectly, when both are present in the same sub-cellular compartment. In these embodiments, the binding of the molecules will enhance complementation between the reduced affinity reporter subunits attached to the molecule of interest and the sub-cellular compartment localized protein.

In certain other embodiments, the molecule of interest and the sub-cellular compartment localized molecule do not directly associate (or bind) with one another, either directly or indirectly, when present in the same sub-cellular compartment. In these embodiments, the complementation between the reporter subunits is driven by the local concentration (or proximity) of the subunits in the sub-cellular compartment. For example, the sub-cellular compartment localization of interest may occur in a membrane, e.g., the endosomal membrane, where the complementing subunits are confined to a relatively small region within the cell, thereby enhancing complementation in the absence of a direct binding interaction.

As mentioned above, the reporter subunits are stably associated to the molecule of interest and the sub-cellular compartment localized molecule. In certain embodiments, the stable association is either direct or via a linker, where the linkage may or may not be a covalent linkage. For example, when the reporter subunits, molecule of interest and the sub-cellular compartment localized molecule are proteins, they may be linked by methods known in the art for linking peptides, e.g., expressed from a nucleic acid sequence as a fusion protein, as reviewed in greater detail below.

A given cell employed in a method of the invention can be provided using any convenient protocol. For example, conjugates of the different molecules and reporter subunits can be introduced into a cell using a number of different protocols, e.g., microinjection, electroporation or a variety of bulk-loading techniques, or by providing in the cell nucleic acids that encode the different elements, e.g., in the form of fusion proteins.

In certain embodiments, the reporter subunit and the molecule of interest (or the sub-cellular compartment localized molecule) may make up a fusion protein that includes a reporter subunit, e.g., a variant minimal N-terminal β galactosidase peptide or a ω peptide as reviewed above. The fusion protein can thus be expressed from an encoding nucleic acid intracellularly. This system is advantageous in certain embodiments because it permits the detection and quantitation of sub-cellular compartment localization in cells, such as mammalian cells, based on enzymatic complementation of the reporter subunits. For example, in an embodiment in which chimeric fused proteins are produced intracellularly that include a sub-cellular compartment localized protein (or peptide) fused to a first reporter subunit and a "test" protein of interest fused to a second reduced affinity complementing reporter subunit, the detected activity due to sub-cellular compartment localization between the chimeric proteins will be proportional to the amount of the "test" fusion protein associated with the same sub-cellular compartment as the sub-cellular compartment localized fusion protein. In certain embodiments, the molecule of interest and the sub-cellular compartment localized protein bind to one another, either directly or indirectly, when associated with the same sub-cellular compartment. In these embodiments, this interaction can increase the amount of complementation (and enzyme activity) by driving association between the reduced affinity reporter subunits. However, direct or indirect interaction between the molecule of interest and the sub-cellular compartment localized molecule when co-localized to the same sub-cellular compartment is not a necessary feature of the systems and methods of the present invention. Enzyme activity can be produced when the molecule of interest and the sub-cellular compartment localized molecule are in close proximity. In certain embodiments, the fusion gene constructs are constructed and transformed into cells to produce a first, e.g., low, level expression, where this low level expression is the result of the non-binding moiety mediated reversible association of the reporter subunits. The system then permits the monitoring of interactions in a given cell in the presence of endogenous competing protein partners, where the fusion protein will function as a "tracer" for the binding/association reaction. Such a system is not prone to artifacts arising from over-expression of introduced proteins. Reduction in expression of fusion gene constructs can be accomplished by choice of appropriate promoters, ribosome binding sites and other regulatory elements. For example, fusion gene constructs can be introduced into vectors in which they lie upstream of an antibiotic resistance gene whose translation is regulated by the Encephalomyocarditis virus internal ribosome entry sequence (IRES), and which contain a mutation in the splice donor/acceptor sequences upstream of the ATG sequence responsible for translational initiation of the fusion gene. This type of construct results in a lower translation efficiency of the first coding sequence in a bicistronic message, but does not affect translation of the second (antibiotic resistance) sequence, which is solely dependent on the IRES. As a result of these reduced levels of expression, the frequency of spontaneous interaction of reporter subunits, which is concentration-dependent, will be significantly reduced.

Fusion proteins of embodiments of the invention include a single continuous linear polymer of amino acids which includes the full or partial sequence of two or more distinct proteins, i.e., a protein of interest and a sub cellular compartment localized protein. Two or more amino acid sequences may be joined chemically, for instance, through the intermediacy of a cross-linking agent. In certain embodiments, a fusion protein is generated by expression of a fusion gene construct in a cell. A fusion gene construct includes a single continuous linear polymer of nucleotides which encodes the full or partial sequences of two or more distinct proteins in the same uninterrupted reading frame. Fusion gene constructs also may contain replication origins active in eucaryotic and/or procaryotic cells and one or more selectable markers encoding, for example, drug resistance. They may also contain viral packaging signals as well as transcriptional and/or translational regulatory sequences and RNA processing signals.

In certain embodiments, the fusion gene constructs of the invention are introduced into cells to assay for sub-cellular compartment co-localization of the fusion proteins encoded by the fusion gene constructs. The fusion gene constructs may also contain promoters and other transcriptional and/or translational regulatory sequences that are normally associated with the gene encoding the putative binding moiety. The fusion gene constructs may be introduced into cells by any method of nucleic acid transfer known in the art, including, but not limited to, viral vectors, transformation, co-precipitation, electroporation, neutral or cationic liposome-mediated transfer, microinjection or gene gun. Viral vectors of interest include, but are not limited to: retroviruses, poxviruses, herpesviruses, adenoviruses, and adeno-associated viruses. In certain embodiments, retroviral vectors are employed, which are capable of stable integration into the genome of the host cell. For example, retroviral constructs encoding integration and packaging signals, drug resistance markers and one or more fusion genes of interest are useful in the practice of embodiments of the invention.

Different fusion gene constructs encoding unique fusion proteins may be present on separate nucleic acid molecules or on the same nucleic acid molecule. In certain embodiments, the same vector is employed so that uptake of only a single species of nucleic acid by a cell is sufficient to introduce sequences encoding both putative binding partners into the cell. In terms of order of introduction, in those embodiments where the coding sequences are on different vectors, the vectors may be introduced into the cell simultaneously or sequentially.

The fusion gene constructs or fusion proteins of the invention may be introduced into cultured cells, animal cells in vivo, animal cells ex vivo, or any other type of cell in which it is desired to study sub-cellular compartment localization.

Following provision of the cell comprising the molecule of interest and the sub-cellular compartment localized molecule each tagged (i.e., labeled) with a different subunit of the reporter system, the cell is then evaluated for activity of the reporter system, where the result of this evaluation step provides information about whether a sub-cellular compartment localization event of interest has taken place. In certain embodiments, evaluation includes detecting the activity and then comparing the observed activity to a reference or control value, e.g., a previously determined background activity value, such as a level of β-galactosidase activity that is observed in a cell in which the reporter subunits are not co-localized to the same sub-cellular compartment (e.g., when the reporter subunits are fused to proteins that reside in distinct sub-cellular compartments), also called a background level. As developed in more detail below, evaluation may include observing activity at two or more times during a given observation period, e.g., before and after contact of the cell with a test agent, etc., as may be required by a given assay protocol. This evaluation step may include providing a suitable substrate for the enzyme of the system, and detecting the enzyme mediated production of a detectable product therefrom, as developed in more detail below.

The reporter systems disclosed herein may be used to assay sub-cellular compartment co-localization of molecules attached to reporter subunits through complementation between the reporter subunits which produce a detectable signal. In addition to testing for sub-cellular compartment co-localization of a molecule of interest and a sub-cellular compartment localized molecule, the subject invention provides for determining sub-cellular compartment localization of molecules that is dependent upon one or more additional molecules or ions, e.g., small molecules, ligands, drugs, peptides, pharmaceuticals, etc.

In one embodiment, the sub-cellular compartment localization of one (or more) moiety may be measured by providing a reporter system including one component having a first moiety bound to a first reporter subunit and at least a second component including a different moiety bound to a second reporter subunit, where the sub-cellular compartment localization of the second component in known (i.e., the different moiety has a known sub-cellular compartment localization when present in a cell). In the system, the reporter subunits are capable of associating and forming an active enzyme that can generate a detectable signal (e.g., by the activity of the enzyme on a cognate substrate) only if they are brought into proximity to one another, e.g., by being associates with the same sub-cellular compartment. The signal can be directly or indirectly detected and quantitated, e.g., by comparing the signal to a control value (e.g., obtained in a suitable control assay).

In one embodiment of the invention, sub-cellular compartment co-localization can be detected and quantitated. The signal produced by the complementing reporter subunits can serve as an indicator of co-localization to a sub-cellular compartment, either directly or indirectly via a third substance. Signals which could be detected include light emission and absorbance. Exemplary signals include chromogenic, fluorescent and luminescent signals. These signals can be detected and quantitated visually or through the use of flow cytometers, spectrophotometers, fluorimeters, microscopes, scintillation counters or other instrumentation known in the art.

Association of components of the reporter systems disclosed herein will depend upon factors in solution, such as pH, ionic strength, concentration of components of the assay, and temperature. Assay solutions can be designed and developed for a particular system. The reporter systems disclosed herein can be used to conduct assays in solutions, such as buffered cell free solutions, cell interiors, solutions of cells, solutions of cell lysates, and solutions of cell fractions, such as nuclear fractions, cytoplasmic fractions, mitochondrial fractions, and membrane fractions. Methods for preparing assay solutions, such as enzyme assay solutions, cell extracts, and cell suspensions, known in the art may be used. For example, physiologically compatible buffers such as phosphate buffered saline may be used. See for example, the series, Methods in Enzymology, Academic Press, New York.

In one embodiment, the reporter subunits are capable of complementing one another to form an enzymatically active complex that is capable of catalyzing the conversion of a substrate to a product which is detectable, either directly or indirectly. In one embodiment, the reporter system can include two or more components, each of which is a fusion protein, wherein the fusion proteins each comprise a protein (or polypeptide) fused to a low affinity reporter subunit. Thus, nucleic acids encoding the fusion proteins can be constructed, introduced into cells and expressed in cells. Alternatively, the presence of the complementing reporter sub-units can be detected by detecting the binding of a labeled specific binding moiety, such as an antibody, to the associated complementing reporter subunits.

In one embodiment, the low affinity reporter subunits may be complementing subunits of β-gal, as reviewed above. The system may include two, three or more reporter subunits, all of which are required to associate in order to produce the detectable signal. Methods for detecting the reaction products of active β-gal that have been developed in the art may be used. For example, β-galactosidase activity may be measured by a range of methods including live-cell flow cytometry and histochemical staining with the chromogenic substrate 5-bromo-4-chloro-3-indolyl β-D-galactopyranoside (X-Gal). Nolan et al., Proc. Natl. Acad. Sci, USA, 85:2603-2607 (1988); and Lojda, Z., Enzyme Histochemistry: A Laboratory Manual, Springer, Berlin, (1979). Histochemical staining for β-gal can be achieved by fixation of cells followed by exposure to X-gal.

In certain embodiments, β-galactosidase activity is detected using a luminescent enzyme prosubstrate, e.g., a luciferase prosubstrate, where the prosubstrate includes both a luminescent enzyme substrate domain (e.g., luciferase substrate domain, acquorin substrate domain, etc.) and a reporter enzyme cleavable domain that, upon contact with the reporter enzyme, is separated (i.e., cleaved) from the luminescent enzyme substrate domain to produce free luminescent enzyme substrate (e.g., luciferase substrate), where the free substrate can then be converted by a luminescent enzyme, e.g., luciferase, to a luminescent product. As such, in these embodiments, a second enzyme activity is present in the reaction which acts upon the luminescent enzyme substrate domain (e.g., the luciferin) released from the prosubstrate by the activity of β-galactosidase.

In certain embodiments, the prosubstrate is a conjugate of the luciferase substrate domain and the reporter enzyme cleavable domain. In certain embodiments, the prosubstrate is capable of passing through a cell membrane. In certain embodiments, the size of the prosubstrate is small. As such, the molecular weight of the prosubstrate in certain embodiments is at least about 100 D, such as at least about 400 D and including at least about 500 D, and may be as great as 2000 D or greater, but in certain embodiments does not exceed about 5000 D. In certain embodiments, the prosubstrate exhibits low toxicity, where by low toxicity is meant that the substrate is substantially no more toxic than D-luciferin, where a given substrate is considered to be substantially no more toxic than D-luciferin. In representative embodiments, the $LD_{50}$ of the prosubstrate does not exceed about 5000 mg/kg, and in certain embodiments does not exceed about 1000 mg/kg, and in certain embodiments does not exceed about 20000 mg/kg (for description of $LD_{50}$, see, e.g., the Canadian Center for Occupational Health and Safety at www(dot) ccohs(dot)ca(slash) oshanswers(slash)chemicals(slash)ld50).

The luciferase substrate domain of the prosubstrate may be any convenient luciferase substrate. In certain embodiments, the luciferase substrate domain is a luciferin compound, i.e., a luciferin or a derivative thereof. Luciferins and luciferin derivatives of interest include, but are not limited to: those described in U.S. Pat. Nos. 5,374,535; 5,374,534; 5,128,069; 5,098,828; and 4,826,989; the disclosures of which compounds are herein incorporated by reference.

The reporter enzyme cleavable domain of the prosubstrate may be any convenient moiety, so long as its presence in the prosubstrate at least impairs, if not completely impedes or inhibits, the ability of the luciferase substrate domain from acting as a substrate for luciferase. In certain embodiments, the cleavable domain is one that sterically hinders the ability of luciferase to use the luciferase substrate domain as a substrate, such that the size of the cleavable domain may range from about 10 daltons to about $10.\sup.5$ daltons (i.e., 100 kilodaltons), such as from about 100 daltons to about 50 kilodaltons, including from about 1000 daltons to about 10,000 daltons. The particular nature of the cleavable domain depends on the nature of the reporter enzyme whose activity is to be evaluated.

In certain embodiments, β-galactosidase activity is detected using prosubstrates that includes a D-luciferin domain conjugated to a galactosidase substrate domain, where in certain embodiments the substrate is D-luciferin-O-β-galactopyranoside (also known as LuGal). A description of luminescent enzyme prosubstrates that found use in the present invention can be found in U.S. application Ser. No. 11/706,838, filed on Feb. 14, 2007 (publication no. 2007/0224621), incorporated herein by reference for its description of such prosubstrates and their use in reporter assays.

In certain embodiments, detection of β-galactosidase complementation using luminescent enzyme prosubstrates is performed in intact target cells. In these embodiments, the cells contain a luminescent enzyme (e.g., luciferase) specific for the luminescent enzyme substrate portion of the prosubstrate. For example, the cell can express a luciferase from an exogenous expression cassette (viral, plasmid, as a transgene in an intact animal, etc.).

Contact of the prosubstrate and cell may occur in an in vitro or in vivo format. In vitro formats of interest include cell-based formats, in which contact occurs e.g., by introducing the substrate in a medium, such as an aqueous medium, in which the cell is present. In yet other embodiments, the assay may be in vivo, in which a multicellular organism that includes the cell is employed, and the prosubstrate is contacted with the cell containing multicellular organism. Contact of the targeting vector with the target cell(s) may be accomplished using any convenient protocol. In those embodiments where the target cells are present as part of a multicellular organism, e.g., an animal, the prosubstrate is conveniently administered to (e.g., injected into, fed to, etc.) the multicellular organism, e.g., a whole animal, where administration may be systemic or localized, e.g., directly to specific tissue(s) and/or organ(s) of the multicellular organism. In certain embodiments, the prosubstrate is intraperitoneally administered to the animal.

Multicellular organisms of interest include, but are not limited to: insects cell, vertebrates, such as avian species, e.g., chickens; mammals, including rodents, e.g., mice, rates; ungulates, e.g., pigs, cows, horses; dogs, cats, primates, e.g., monkeys, apes, humans; and the like. As such, the target cells of interest include, but are not limited to: insects cells, vertebrate cells, particularly avian cells, e.g., chicken cells; mammalian cells, including murine, porcine, ungulate, ovine, equine, rat, dog, cat, monkey, and human cells; and the like.

Following contact of the prosubstrate and the target cell(s), the activity of the reporter enzyme is evaluated or assessed by detecting the presence or absence of signal from luciferase substrate, i.e., by screening the cell (either in vitro or in vivo) for the presence of a luciferase mediated luminescent signal. The detected signal is then employed to evaluate the activity of the reporter enzyme, since the presence of a detected signal is dependent upon an underlying activity of the reporter enzyme.

The luminescent signal produced by the luciferase mediated conversion or the reporter enzyme released luciferase substrate of the prosubstrate may be detected using any convenient luminescent detection device. In certain embodiments, detectors of interest include, but are not limited to: photo-multiplier tubes (PMTs), avalanche photodiodes (APDs), charge-coupled devices (CCDs); complementary metal oxide semiconductors (CMOS detectors) and the like. The detector may be present in a signal detection device, e.g., luminometer, which is capable of detecting the signal once or a number of times over a predetermined period, as desired. Data may be collected in this way at frequent intervals, for example once every 10 ms, over the course of a given assay time period.

In certain embodiments, the methods are employed in an in vivo bioluminescent imaging protocol, where such protocols include, but are not limited to, those described in U.S. Pat. Nos. 6,939,533; 6,923,951; 6,916,462; 6,908,605; 6,890,515; 6,649,143; 6,495,355; 6,217,847; and 5,650,135, incorporated herein by reference for their description of such in vivo bioluminescent assays. In such embodiments, the methods may include immobilizing a multicellular animal that includes the subject cell(s) and prosubstrate, and then detecting signal from the animal using whole animal imaging techniques.

In certain embodiments, the assay for β-gal activity may be performed on lysates from the cells under study. In certain of these embodiments, the cells may be contacted with a cross-linking agent that binds the two reduced affinity reporter subunits together when they are present in close proximity to one another in the cell, i.e., in the same sub-cellular compartment. In this way, the reduced affinity subunits will remain in association with each other during the course of the detection step of the assay in which the sub cellular compartment no longer exists. In certain of these embodiments, the cells are permeabilized to allow access of the cross-linking agent to the interior of the cell. In certain other embodiments, permeabilization and/or contacting with a cross-linking (or fixation) agent may be employed in assays in which the cells are not lysed, thereby maintaining the integrity of the sub-cellular compartment of interest. In certain embodiments where the molecule of interest and the sub-cellular compartment localized molecule are binding partners, cross-linking may not be necessary when employing a cell-lysate based detection assay. In certain embodiments, the most appropriate detection assay for the particular cell and reporter components used is determined empirically.

Assays for β-gal activity as described in Mohler and Blau, Proc. Natl. Acad. Sci., 93:12423-12427 (1996), may be used. In one embodiment, intracellular analyses may be conducted by fixing cells and staining with the indigogenic substrate X-gal. Fixed cells also can be analyzed by assaying for β-gal activity by fluorescence histochemistry using an azo dye in combination with either X-gal or 5-bromo-6-chloro-3-indolyl β-D-galactopyranoside (5-6-X-Gal). A combination of interest is the azo dye red violet LB (Sigma Chemical, St. Louis, Mo.) and 5-6-X-Gal, referred to as Fluor-X-gal. For this combination, fluorescence micrographs can be obtained on a fluorescence microscope using a rhodamine/Texas Red filter set. Use of these substrates allows for β-gal-dependent fluorescence to be visualized simultaneously with two or more other fluorescent signals.

Vital substrates for β-gal, which can be used in living cells, are also encompassed by the invention. For example, a vital fluorogenic substrate, resorufin β-galactoside bis-aminopropyl polyethylene glycol 1900 (RGPEG) has been described. Minden (1996) BioTechniques 20(1):122-129. This compound can be delivered to cells by microinjection, electroporation or a variety of bulk-loading techniques. Once inside a cell, the substrate is unable to escape through the plasma membrane or by gap junctions. Another vital substrate that can be used in the practice of the invention is fluorescein di-β-D-galactopyranoside (FDG), which is especially well-suited for analysis by fluorescence-activated cell sorting (FACS) and flow cytometry. Nolan et al. (1988) Proc. Natl. Acad. Sci. USA 85:2603-2607 and Rotman et al. (1963) Proc. Natl. Acad. Sci. USA 50:1-6.

β-gal may also be detected using a chemiluminescence assay. For example, cells containing β-gal fusions are lysed (with or without contacting with a crosslinking agent) in a mixture of buffers containing Galacton Plus substrate from a Galactolight Plus assay kit (Tropix, Bedford Mass.). Bronstein et al, J. Biolumin. Chemilumin., 4:99-111 (1989). After addition of Light Emission Accelerator solution, luminescence is measured in a luminometer or a scintillation counter.

Representative substrates that are suitable for spectrophotometric or fluorometric analysis include, but are not limited to: p-aminophenyl-β-D-galactopyranoside; 2'-N-(hexadecanol)-N-(amino-4'-nitrophenyl)-β-D-galactopyranoside; 4-methylumbel-liferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galacto-pyranoside, 5-bromo-4-chloro-3-indolyl-β-D-galactopynanosiredse, resorufin-β-D-galactopyranoside, 7-hydroxy-4-trifluoromethyl coumarin, Ω-nitrostyryl-β-D-galactopyranoside, and flourescein-β-D-galactopyranoside. See, e.g., U.S. Pat. No. 5,444,161.

Reporter systems other than β-gal may also be used in the practice of the invention. For example, the enzyme β-glucuronidase (GUS) can be used as a reporter and chromogenic and fluorogenic GUS substrates have been developed. The GUS substrate 5-bromo-4-chloro-3-indolyl β-D-glucuronic acid (X-gluc) can be used in both chromogenic and fluorogenic applications, as follows. In one method of chromogenic staining, fixed cells are washed in PBS and stained with 2 mM X-gluc (Molecular Probes, Eugene Oreg.), 10 mM EDTA, 0.5 mM $K_3Fe(CN)_6$, 0.5 mM $K_4Fe(CN)_6$, 0.1% Triton X-100, 0.1 M $NaPO_4$. Fluorogenic staining may be achieved by using a combination of 5-bromo-6-chloro-3-indolyl β-D-glucuronic acid (5, 6 X-gluc, Molecular Probes, Eugene, Oreg.) and Fast Red Violet LB (Sigma Chemical, St. Louis, Mo.). Fixed cells are rinsed with PBS and stained in 50 µg/ml 5, 6 X-gluc and 100 µg/ml Fast Red Violet LB, then rinsed in PBS. Fluorescence is detected on a fluorescence microscope adjusted for detection of rhodamine fluorescence. In one embodiment of the invention, the reporter subunits include an enzyme and an inhibitor of the enzyme. In these embodiments, the inhibitor has a low affinity for the enzyme. In this case, association between the putative binding moieties is evidenced by inhibition of the activity of the enzyme. Exemplary enzymes include β-gal, GUS, β-lactamase, etc.

The methods disclosed herein enable the detection and quantitation of sub-cellular compartment co-localization events in cell lysates, as well as in intact cells. Thus, interactions between fully folded proteins are detectable, and co-translational expression of the binding moieties is not necessary for binding to be detected.

In the practice of the invention, the reaction product may be detected indirectly, for example, through immunological techniques, such as immunofluorescent labeling.

Sub-cellular compartment co-localization of proteins can be measured in a reporter system of the invention which includes one or more fusion proteins. The fusion proteins each include a protein domain (e.g., a "test" fusion protein or a sub-cellular compartment localized protein) coupled to a subunit of a low affinity reporter system. For intracellular expression of the fusion proteins, one or more fusion gene constructs are prepared which include sequences encoding the fusion protein(s). The fusion gene constructs may be introduced into cells by methods available in the art, including, but not limited to, viral vectors, transformation, co-precipitation, electroporation, neutral or cationic liposome-mediated transfer, microinjection or gene gun.

A variety of cell-based assays can be conducted using the cells containing the fusion gene constructs. Sub-cellular compartment co-localization of the fusion proteins expressed in the cells can be confirmed by detecting the signal produced by the reporter subunits undergoing complementation when in close proximity, i.e., associated with the same sub-cellular compartment. Thus, for example, when the reporter subunits are complementing β-gal subunits, cells exhibiting β-gal activity indicate sub-cellular compartment co-localization of the moieties within those cells.

The fusion gene constructs may also contain promoters and other transcriptional and/or translational regulatory sequences that are normally associated with the gene encoding the moiety of interest. This permits the study of physiologically-relevant levels of the proteins in vivo, in contrast to systems in which test proteins are overexpressed. Further, this permits the study of naturally-occurring changes in levels of sub-cellular compartment co-localization over time and can reveal the effects of endogenous or exogenous substances on co-localization.

The methods and compositions of the invention can also be used to study other molecules which influence the sub-cellular compartment co-localization of the molecules of interest, e.g., in screening assays, including high-throughput screening assays. Proteins, peptides, nucleic acids, carbohydrates, lipids, ions, small molecules, synthetic compounds or other substances (either endogenous to the cell or exogenously added) may act as either promoters or inhibitors of a sub-cellular compartment co-localization event. By measuring the effect of such molecules on, for example, β-gal activity produced by cells containing two or more fusions representing a particular pair of test proteins, the activity of such molecules on sub-cellular compartment co-localization of the molecules of interest can be determined. Use of the methods and compositions of the invention will allow high-throughput assays to be carried out to test for agents that impact sub-cellular localization of a molecule of interest. Such high-throughput assays will be especially valuable in screening for drugs that influence medically-relevant sub-cellular compartment co-localization events.

In certain embodiments, high throughput assays employing the methods and compositions of the invention have favorable Z-factors. The Z-factor is a measure of the quality or power of a high-throughput screening (HTS) assay (see Zhang et al, *A Simple Statistical Parameter for Use in Evaluation and Validation of High Throughput Screening Assays*, 4(2) J. Biomol. Screen. 67-73 (1999), for a full description of Z factors; this reference is incorporated by reference herein in its entirety for its description of Z factors).

One (but not the only) formula for calculating the Z factor of an assay is as follows, where the mean (μ) and standard deviation (σ) of both the positive (p) and negative (n) controls are $\mu_p$, $\sigma_p$, $\mu_n$, and $\sigma_n$, respectively:

$$Z \text{ factor} = 1 - \frac{3 \times (\sigma_p + \sigma_n)}{|\mu_p - \mu_n|}$$

The closer an assay's Z factor is to the ideal value of 1.0 (they cannot be greater than 1), the better it is suited for use in high throughput screens. In general, any assay having a positive Z factor can be used for high throughput screening. In Zhang et al., a Z factor is considered excellent if it is about 0.5 or greater. As such, in certain embodiments, assays that employ the methods and compositions of the subject invention have Z factors that are about 0.1 or greater, about 0.2 or greater, about 0.4 or greater, about 0.5 or greater, about 0.6 or greater, about 0.8 or greater, and up to about 0.9 or greater.

In certain embodiments, substances or agents which influence sub-cellular compartment localization can include those which directly or indirectly affect an upstream event which results in the translocation of a molecule from one sub-cellular compartment to another. For example, if phosphorylation of the molecule of interest (or "test" molecule) endows it with the capacity to translocate to a specific sub-cellular compartment, substances which influence the sub-cellular compartment localization of the molecule of interest include those which directly or indirectly affect a kinase activity.

Assays can be developed as disclosed herein to examine the effect on sub-cellular compartment localization of a molecule of interest in response to a variety of compositions, including drugs such as antipyretic and anti-inflammatory drugs, analgesics, antiarthritics, antispasmodics, antidepressants, antipsychotics, tranquilizers, antianxiety drugs, narcotic antagonists, antiparkinsonism agents, cholinergic antagonists, chemotherapeutic agents, immunosuppressive agents, antiviral agents, parasiticides, appetite suppressants, antiemetics, antihistamines, antimigraine agents, coronary vasodilators, cerebral vasodilators, peripheral vasodilators, hormonal agents, contraceptives, antithrombotic agents, diuretics, antihypertensive agents, cardiovascular drugs, opioids, and vitamins.

The kinetics of sub-cellular compartment localization also can be studied. For example, kinetics of sub-cellular compartment localization can be determined by measuring β-gal activity at different times following addition of an agent to cultures of cells expressing first and second reporter subunit fusions (as described above). A dose-response curve can also be obtained, in which the extent of sub-cellular compartment localization, as measured by β-gal activity, is determined as a function of agent concentration. This assay can be adapted to control for the possible effect of a protein component on its fusion partner, thereby enabling the study of sub-cellular compartment localization in a quantitative fashion.

The reporter system can also be designed with controls to permit the quantitation of the expression level of the β-gal fusion proteins. This will make it possible to control for potential differential expression of the two (or more) fusion proteins. For example, a peptide tag for which well-characterized monoclonal antibodies are available may be fused in frame at the C-terminus of each β-gal mutant. Different tags, such as flag, HA and myc may be used for the different subunits, to allow differential detection of the two mutants even when coexpressed in the same cells. In parallel with the determination of β-gal activity in the lysates of these cells, an ELISA assay can determine the precise amount of each β-gal fusion protein in the same lysates. First, a polyclonal anti-β-gal antiserum may be used to immobilize the antigens. Then the monoclonal antibody directed against the appropriate tag followed by an enzyme-linked anti-mouse secondary antibody may be used to quantify the amount of the β-gal fusion protein of interest. Such an approach, employing well-characterized techniques, should allow a determination of the expression levels of each fusion protein. This modification will be useful where the attached tag does not itself alter the sub-cellular compartment localization of the protein or the ability of the reporter subunits to complement.

In certain embodiments, the subject methods are performed in a high throughput (HT) format. In certain of these embodiments, a plurality of different compounds are tested simultaneously by contacting the compounds to cells comprising sub-cellular localization fusion proteins followed by detecting their co-localization in response to the contacting, (e.g., as compared to a control sample as described in detail above). By simultaneously tested is meant that each of the compounds in the plurality are tested at substantially the same time. Thus, at least some, if not all, of the compounds in the plurality are assayed for their effects in parallel. The number of compounds in the plurality of that are simultaneously tested is typically at least about 10, where in certain embodiments the number may be at least about 100 or at least about 1000, where the number of compounds tested may be higher. In general, the number of compounds that are tested simultaneously in the subject HT methods ranges from about 10 to 10,000, usually from about 100 to 10,000 and in certain embodiments from about 1000 to 5000.

A variety of high throughput screening assays for determining the activity of candidate agent are known in the art and are readily adapted to the present invention, including those described in e.g., Schultz (1998) Bioorg Med Chem Lett 8:2409-2414; Weller (1997) Mol. Divers. 3:61-70; Fernandes (1998) Curr Opin Chem Biol 2:597-603; Sittampalam (1997) Curr Opin Chem Biol 1:384-91; as well as those described in published United States applications 20040072787 and 20060057557 and issued U.S. Pat. Nos. 6,127,133; 6,127,133; 6,372,183; and 7,060,445; the disclosures of which are herein incorporated by reference.

For example, in certain embodiments, high-throughput assays of the invention are conducted using a high-throughput assay device, which in certain embodiments is an automated high-throughput assay device. In these embodiments, the device is loaded with cells comprising the sub-cellular localization fusion proteins of interest, e.g., in separate wells of one or more multiwell plates (as are known in the art), contacted to a plurality of candidate agents (e.g., in a substantially parallel manner as described above), and analyzed for co-localization of the fusion proteins of interest employing any convenient detection assay, e.g., as described in detail above.

Testing of a candidate agent according to the invention as described above readily determines whether the fusion proteins are present in the same sub-cellular compartment. In certain embodiments, an assay according to the present invention detects changes in the sub-cellular localization over time, where the level of sub-cellular localization that is observed may be an increase or a decrease, e.g., over a control assay (e.g., in which no candidate agent is contacted to the cells employed in the assay). In other words, a candidate agent may enhance or inhibit sub-cellular localization of the fusion proteins in the cells. By enhance is meant that the sub-cellular localization of the fusion proteins is increased by at least about 2 fold, usually by at least about 5 fold and sometimes by at least 25, 50, 100 fold and in particular about 300 fold or higher, as compared to a control, i.e., sub-cellular localization of the fusion proteins in cells not contacted with the agent in question. Alternatively, in cases where sub-cellular localization of the fusion proteins is so low that it is undetectable, sub-cellular localization of the fusion proteins is considered to be enhanced if it is increased to a level that is easily detectable. By inhibit is meant that the sub-cellular localization of the fusion proteins is decreased by at least about 2 fold, usually by at least about 5 fold and sometimes by at least 25, 50, 100 fold and in particular about 300 fold or higher, as compared to a control, i.e., sub-cellular localization of the fusion proteins that is not contacted with the agent in question. Other control assays may be employed in the assays of the present invention, including, but not limited to, controls in which only one of the fusion proteins is expressed in the cells; controls in which non-functional mutants (or constitutively active mutants) of one or both of the fusion proteins are employed; controls in which agents with known activities are employed (e.g., agents either not affecting, enhancing or inhibiting sub-cellular localization of the fusion proteins); etc.

Utility

Embodiments of the invention can be used in a broad range of studies of sub-cellular compartment localization to be carried out quantitatively or qualitatively in living cells. In what follows, non-limiting examples of different applications of the methods of the invention are provided.

The methods of the invention can be used to screen for proteins that alter the sub-cellular compartment localization of a molecule of interest. In this embodiment, the protein of interest, fused to a first reporter subunit, is stably expressed in a well-characterized cell line along with a sub-cellular compartment localized protein fused to a second low affinity subunit. Expression libraries containing cDNAs are introduced into these cells using, for example, retroviral vectors (e.g., Kitamura et al., Proc Natl. Acad. Sci. USA 92:9146-9150 (1995)) or any other means of gene transfer known in the art. Vectors expressing gene products that alter the sub-cellular compartment localization the first fusion protein in relation to the second fusion protein, i.e., decreasing or increasing its targeting to the sub-cellular compartment of interest, are isolated by identifying positive clones, i.e., clones that have altered activity relative to control cells expressing the two fusion proteins. An advantage of this system is that the screen can be carried out in any cell type, regardless of the cell's milieu of endogenous (and potentially competing) proteins. The use of fluorescence-activated cell sorting techniques is particularly well-suited to this embodiment of the invention. For example, β-gal-positive cells which contain cDNAs expressing gene products that promote the targeting of the fusion protein of interest to a particular sub-cellular compartment will generate a signal that will allow such cells to be purified by cell-sorting techniques. Conversely, β-gal-negative cells (from cells that are β-gal-positive under control conditions), may also be isolated. Such cDNAs could be delivered, for example, using retroviral vectors that allow introduction of high complexity cDNA libraries with high infection efficiency.

The assays and methods of the invention can also be carried out in the presence of extracellular signaling molecules, growth factors or differentiation factors, peptides, drugs or synthetic analogs, or the like, whose presence or effects might alter the sub-cellular compartment localization of the protein of interest in a particular cell type. For example, the methods and compositions of the invention find use in assays for the internalization and trafficking of cell surface receptors to the endosomal compartment of a cell in response to signal transduction (e.g., binding of a cognate ligand). Exemplary receptors that can be studies include G-protein coupled receptors, as discussed in more detail in the Experimental section.

In certain embodiments, the subject methods of the invention are employed with cDNA libraries, e.g., cDNA libraries in retroviruses, to identify proteins that co-localize with a specific test protein having a known sub-cellular compartment localization in mammalian cells. For this application, construction of cDNA libraries include cDNA coding sequences fused to a sequence encoding a first reporter subunit will be used, e.g., where it is present in a retroviral vector. Testing will be conducted by introducing the cDNA library into cells, e.g., via retroviral infection, cells expressing the second reporter component, e.g., the protein known to localize to a specific sub-cellular compartment fused with the second reporter domain. Those test proteins which are capable of co-localizing with the protein of interest will allow detection of a reporter signal in cells in which they are co-expressed In one embodiment of the invention, cells in which a protein encoded by the cDNA vectors is able to interact with the sub-cellularly localized protein of interest are detected and isolated by flow cytometry or fluorescence-activated cell sorting (FACS). Methods for flow cytometry and FACS are well-known in the art; e.g., Nolan et al. (1988) Proc. Natl. Acad. Sci. USA 85:2603-2607; Webster et al., Exp. Cell Research, 174:252-265 (1988); and Parks et al. (1986) in The Handbook of Experimental Immunology, (eds. Weir, D. M., Herzenberg, L. A., Blackwell, C. C. & Herzenberg, L. A.), Blackwell, Edinburgh, 4th edition, pp. 29.1-29.21. In this way, clones of cells in which co-localization occurs can be isolated and propagated for further study. This aspect is particularly suited for studies of developmental mechanisms, wherein it is possible to select a population of cells in which a particular developmentally-relevant sub-cellular compartment localization event has occurred and study the further development of that cell population, while at the same time, studying the further development of cells in which the sub-cellular compartment localization event has not occurred, for comparison. In a similar fashion, the practice of the invention makes it possible to isolate and/or study the further development of cells exhibiting sub-cellular compartment localization of proteins such as transcriptional regulatory proteins, translational regulatory proteins, DNA replication proteins, mRNA splicing proteins, proteins involved in signal transduction, proteins involved in cell-cell and cell-substrate adhesion (for example, cell movement, axon guidance and angiogenesis), oncogene products, tumor suppressors, proteins involved in cell-cycle control and viral proteins, such as those involved in regulation of viral replication, virus-host interactions and virus assembly, and proteins which are subunits, crosslinkers, modifying agents or molecular motors within the cytoskeleton of cells.

The invention can be used for investigations relating to the localization of specific molecules within intact cells, or intact animals. Types of cells which can be used are primary or established cell lines and other types of embryonic, neonatal or adult cells, or transformed cells (for example, spontaneously- or virally-transformed). These include, but are not limited to fibroblasts, macrophages, myoblasts, osteoclasts, osteoclasts, hematopoietic cells, neurons, glial cells, primary B- and T-cells, B- and T-cell lines, chondrocytes, keratinocytes, adipocytes and hepatocytes.

Processes involving the trafficking or targeting of a molecule of interest to a particular sub-cellular compartment which can be studied in the practice of the invention include, but are not limited to, cell-surface receptor internalization and endosomal targeting (e.g., in response to ligand binding/activation events or during development); nuclear import/export of proteins (e.g., transcription factor trafficking in response to signaling event); antigen uptake, processing and MHC presentation; export of proteins to the extracellular environment, etc. In embodiments in which the effect of signaling events on the sub-cellular compartment localization of a molecule (e.g., a receptor, ligand or transcription factor) are being assayed, exemplary cell stimuli include soluble factors, including leptin and growth factors such as epidermal growth factor (EGF), nerve growth factor (NGF), platelet-derived growth factor (PDGF), and insulin-like growth factors I and II (IGF-I and IGF-II), transforming growth factors α and β (TGF-α and TGF-β), endorphins, prostaglandins, cytokines, chemokines, and neurotransmitters, etc.

Additional cellular processes that can be studied by the practice of the invention include those involved in cell metabolism and cell structure. These include, but are not limited to, interactions that are involved in energy metabolism or which establish or modify the structure of the membranes, cytoplasm, cytoskeleton, organelles, nuclei, nuclear matrix or chromosomes of cells. Co-localization of constituents of the extracellular matrix, or between constituents of the extracellular matrix and cells, can also be studied with the methods and compositions of the invention.

Additional utilities of the subject reduced affinity enzyme complementation reporter systems include, but are not limited to, those described in Published U.S. Patent Application Serial Nos. 20030219848; as well as in U.S. Pat. Nos. 4,378,428; 4,708,929; 5,037,735; 5,106,950; 5,362,625; 5,464,747; 5,604,091; 5,643,734; and PCT application nos. WO96/19732; WO98/06648; WO92/03559; WO01/0214; WO01/60840 and WO 00/039348; the disclosures of which are herein incorporated by reference.

Kits

Also provided by the subject invention are kits for use in practicing one or more of the above described applications. In certain embodiments, kits at least include a cell that expresses, either constitutively or inducibly, one or more fusion proteins that include a sub-cellular compartment localized molecule and a reporter subunit, as reviewed above. In certain embodiments, kits include elements for making such cells, e.g., first and second nucleic acids encoding first and second fusion proteins present on the same or different vectors and/or nucleic acids encoding reporter subunits to which proteins of interest can be fused using standard molecular biology techniques, as reviewed above. The kits may further include one or more additional components which find use in practicing embodiments of the invention, including but not limited to, enzyme substrates, cell growth media, etc.

In certain embodiments, kits of the invention include (a) a cell comprising: (i) a first fusion protein that comprises a first protein and a first β-galactosidase fragment; and (ii) a second fusion protein that comprises a sub-cellular compartment localized protein and a second β-galactosidase fragment; wherein the first and second β-galactosidase fragments have a reduced affinity for each other as compared to wild type β-galactosidase fragments; and (b) a β-galactosidase substrate. In certain embodiments, the one of the β-galactosidase fragments is a variant minimal N-terminal β-galactosidase peptide.

In certain embodiments, kits of the invention include: (a) a first nucleic acid encoding a first β-galactosidase fragment; and (b) a second nucleic acid encoding a fusion protein that comprises a sub-cellular compartment localized protein and a second β-galactosidase fragment; wherein the first and second β-galactosidase fragments have a reduced affinity for each other as compared to wild type β-galactosidase fragments. In certain embodiments the first β-galactosidase fragment is a variant minimal N-terminal β-galactosidase peptide and has a binding affinity for the second β-galactosidase fragment that is lower than a β-galactosidase fragment consisting of amino acids 3 to 92 of *E. coli* wild-type β-galactosidase. In certain embodiments, the first and second nucleic acids are present on vectors (e.g., expression vectors, including viral or plasmid-based expression vectors). In certain embodiments, the first vector comprises a restriction site positioned on the vector such that when a protein coding sequence is inserted into the vector using the restriction site, the vector encodes a fusion protein of the protein and the β-galactosidase fragment. In certain embodiments, the kit further comprises a host cell capable of expressing the encoded proteins (for example when the nucleic acids are introduced into the cells). In certain embodiments, the kit further comprises a β-galactosidase substrate for use in evaluating β-galactosidase activity.

In certain embodiments, kits of the invention include: (a) a nucleic acid encoding a first β-galactosidase fragment; (b) a cell comprising a fusion protein that comprises a sub-cellular compartment localized protein and a second β-galactosidase fragment; wherein the first and second β-galactosidase fragments have a reduced affinity for each other as compared to wild type β-galactosidase fragments. In certain embodiments the first β-galactosidase fragment is a variant minimal N-terminal β-galactosidase peptide and has a binding affinity for the second β-galactosidase fragment that is lower than a β-galactosidase fragment consisting of amino acids 3 to 92 of *E. coli* wild-type β-galactosidase. In certain embodiments, the nucleic acid is present on a vector (e.g., an expression vector). In certain embodiments, the vector comprises a restriction site positioned on the vector such that when a protein coding sequence is inserted into the vector using the restriction site, the vector encodes a fusion protein of the protein and the β-galactosidase fragment. In certain embodiments, the kit further comprises a β-galactosidase substrate.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Reduced Affinity β-galactosidase System

A low affinity enzyme complementation system for monitoring protein translocation within a sub-cellular compartment, as opposed to between sub-cellular compartments, using a β-gal subunit variant was employed in the following experiments. To achieve low affinity complementation, the classic α peptide first described by Jacob and Monod (1961) was truncated and mutated at specific residues based on the crystal structure in order to derive the α peptide (α*) that weakly complements the omega (ω) fragment. To assay inter-compartmental protein movement, one enzyme fragment, ω, was localized in a particular region of the sub-cellular compartment (e.g., the internal surface of the plasma membrane) and the small complementing α* peptide was fused to the protein of interest. The concentration of α* in the immediate vicinity of ω correlated with the amount of enzyme activity obtained in a dose- and time-dependent manner, serving as a genetically encoded biosensor for local protein concentration (T. S. Wehrman, C. L. Casipit, N. M. Gewertz, H. M. Blau, Nat Methods 2, 521 (July, 2005)). Due to their low affinity, the interaction of the α* and ω β-gal fragments is not sufficiently strong to maintain a complemented enzyme. As a result, the β-gal activity obtained at any given time is a measure of the dynamic interaction of the two fragments, a reflection of their local concentration. This reduced affinity system is further described in U.S. application Ser. No. 11/132,764 filed on May 18, 2005, the disclosure of which system and its method of product as described in the experimental section of that application is herein incorporated by reference.

This system has been employed to study the interaction of two proteins, where protein-protein interaction is measured as a function of complementation of low affinity mutant subunits of the β-galactosidase (β-gal) enzyme fused to the receptor proteins. This system is described in provisional U.S. Patent Application Ser. No. 60/782,054 filed on Mar. 13, 2006, which is incorporated herein by reference in its entirety.

This combination of features is not found in other protein interaction detection systems based on energy transfer (Y. Xu, D. W. Piston, C. H. Johnson, Proc Natl Acad Sci USA 96, 151 (Jan. 5, 1999); B. A. Pollok, R. Heim, Trends Cell Biol 9, 57 (February, 1999)) or split enzymes including dihydrofolate reductase (J. N. Pelletier, F. X. Campbell-Valois, S. W. Michnick, Proc Natl Acad Sci USA 95, 12141 (Oct. 13, 1998)), β-lactamase (A. Galarneau, M. Primeau, L. E. Trudeau, S. W. Michnick, Nat Biotechnol 20, 619 (June, 2002); T. Wehrman, B. Kleaveland, J. H. Her, R. F. Balint, H. M. Blau, Proc Natl Acad Sci USA 99, 3469 (Mar. 19, 2002)), luciferase (R. Paulmurugan, S. S. Gambhir, Anal Chem 75, 1584 (Apr. 1, 2003)), and the previously described β-galactosidase (F. Rossi, C. A. Charlton, H. M. Blau, Proc Natl Acad Sci USA 94, 8405 (Aug. 5, 1997); F. Rossi, C. A. Charlton, H. M. Blau, Proc Natl Acad Sci USA 94, 8405 (Aug. 5, 1997)).

As demonstrated in the experiments described below, the low affinity β-galactosidase complementation system finds use in detecting translocation between distinct sub-cellular compartments (e.g., between the cell surface and the endosome).

II. Use of Reduced Affinity β-Galactosidase System to Investigate the Activation and Endosomal Translocation of a GPCR The actions of many extracellular signals are mediated by the interaction of guanine nucleotide-binding regulatory proteins (G proteins) and G-protein coupled receptors (GPCRs). Individual GPCRs activate particular signal transduction pathways through binding to G proteins, which in turn transduce a signal to the cell to elicit a response from the cell. GPCRs are known to respond to numerous extracellular signals, including neurotransmitters, drugs, hormones, odorants and light. The family of GPCRs has been estimated to include several thousands members, fully more than 1.5% of all the proteins encoded in the human genome. The GPCR family members play roles in regulation of biological phenomena involving virtually every cell in the body. The sequencing of the human genome has led to identification of numerous GPCRs; although the ligands and functions of many of these GPCRs are known, a significant portion of these identified receptors are without known ligands. These latter GPCRs, known as "orphan receptors", also generally have unknown physiological roles.

III. Materials and Methods

Plasmids. Fusion protein plasmids were generated by subcloning PCR products into MFG-eYFP-α(H31R)-IRES-CD8 (abbreviated eYFP-α) and pWZL-ω-IRES-neo (abbreviated ω) plasmids, which were designed as previously described (Wehrman, T. S., Casipit, C. L., Gewertz, N. M. & Blau, H. M. (2005) Nature Methods 2, 521-7). The FYVE domain of endofin was generated by RT-PCR from a mouse cell line using the primers 5'-atc gac gga tcc ATG CAG AAA CAA CCT ACA TGG G (SEQ ID NO:7) and 5'-ctg agt caa tgT TTA TTT ATA GTC TCA TAG C (SEQ ID NO:8); this PCR product was cloned N-terminal to eYFP-α or ω using BamHI and MfeI restriction sites. Other FYVE domains were generated similarly by RT-PCR⁻. The β2AR-ω construct was used as previously described (Yan, Y. X., Boldt-Houle, D. M., Tillotson, B. P., Gee, M. A., D'Eon, B. J., Chang, X. J., Olesen, C. E. & Palmer, M. A. (2002) J Biomol Screen 7, 451-9). To generate a β2AR-eYFP-α construct, the eYFP-α fragment was subcloned into the β2AR-ω plasmid using XhoI and HindIII. The Angiotensin receptor 1a was derived by RT-PCR from C57/Bl6 mouse brain RNA using primers for the entire coding sequence, minus the stop codon; it was cloned N-terminally to eYFP-α or ω with MfeI and XhoI. Human Arginine Vasopressin receptor 1a cDNA was purchased from the UMR cDNA Resource Center; PCR products were generated and cloned similarly to the Angiotensin receptor 1a. Finally, to generate fusion proteins with β-arrestin, the full coding sequence of human β-arrestin B2 was PCR amplified from a cDNA clone and inserted into the MfeI-XhoI sites of the ω and eYFP-α vectors.

Cell culture and viral transduction. Virus was produced in the ΦNX ecotropic packaging cell line (P. L. Achacoso and G. P. Nolan, unpublished data) by transient transfection of plasmids using the Lipofectamine 2000 reagent (Invitrogen), according to manufacturer's instructions. Supernatant was applied to C2C12 myoblasts after 12-72 h; cells were then centrifuged for 30 min at 2000 rpm in the presence of 8 μg/ml polybrene (Sigma) after a 15-minute incubation at 37° C. Transduced cells were selected either by antibiotic resistance using 1 μg/ml Geneticin (Invitrogen) or by flow cytometric sorting for eYFP, using a FACSTAR flow cytometer with MoFlo electronics. C2C12 myoblasts were grown in DMEM/20% FBS.

Assays and cell preparation. Isoproterenol, propranolol, angiotensin II, [Arg⁸]-vasopressin, and somatostatin (somatostatin-14) were purchased from Sigma. Vasopressin units were converted from I.U. to molar using data obtained from Raggenbass et al. (Proc Natl Acad Sci USA. 1987 November; 84(21):7778-82). LysoTracker Red and Texas Red-labeled transferrin were purchased from Molecular Probes. The Kinase/Phosphatase Inhibitor Library was purchased from BIOMOL, and the Mechanistic and Diversity Compound Libraries were provided by the Developmental Therapeutics Program of the National Cancer Institute. Cells were plated and grown to confluency in 96-well white tissue culture dishes (Corning Costar), in 100 μl of growth media. Dose-response curves were generated by adding the respective ligand to the media and incubating for 2 h at 37° C. Compound library screening was performed by replicating the compound library into 96-well or 384-well plates using disposable 96- or 384-pin replicators (Genetix) and incubating for 30 min at 37° C. before stimulating cells with ligand for 1 h at 37° C. At the end of the described incubation time, Gal-Screen reagent (Buffer B formulation, Applied Biosystems) was used to assay for β-galactosidase activity, according to manufacturer's protocol; media was aspirated from the plate, and 50 μl (or 25 μl for 384-well plates, without prior media aspiration) of Gal-Screen substrate diluted in lysis buffer was added to each well. Plates were incubated at room temperature for 40 min-1 hour before reading in a TR717 luminometer (Tropix). $EC_{50}$ values were calculated by applying non-linear regression (fitting to the logistic, or Hill, curve) using Prism (GraphPad Software).

Fluorescence microscopy. Cells were grown on 4-well chamber slides (BD Biosciences) or in tissue culture plates (Corning Costar). Texas Red-labeled transferrin was purchased from Molecular Probes and used at 50 μg/ml; cells were incubated in DMEM/transferrin for 30-45 min at 37° C., then fixed in 4% paraformaldehyde before mounting in Fluoromount-G (SouthernBiotech). Fixed or live cells were imaged using a Zeiss laser scanning confocal microscope (LSM510 on an Axiovert 100M).

IV. Results

Design of receptor internalization and receptor activation assays. In order to design an internalization assay for GPCR activation, we exploited the CAPT enzyme complementation technology, which relies on protein proximity to yield complementation of two fragments of β-galactosidase (Wehrman et al. (2005) Enzymatic detection of protein translocation. *Nat Methods* 2, 521-527). The design of the internalization assay utilizes an endosomal 'probe' (one enzyme fragment localized to the cytosolic face of endosomes) and a tag on the GPCR of interest (the other fragment on the GPCR's cytoplasmic tail); this paradigm is shown diagrammatically in FIG. 1a.

Figure 5:
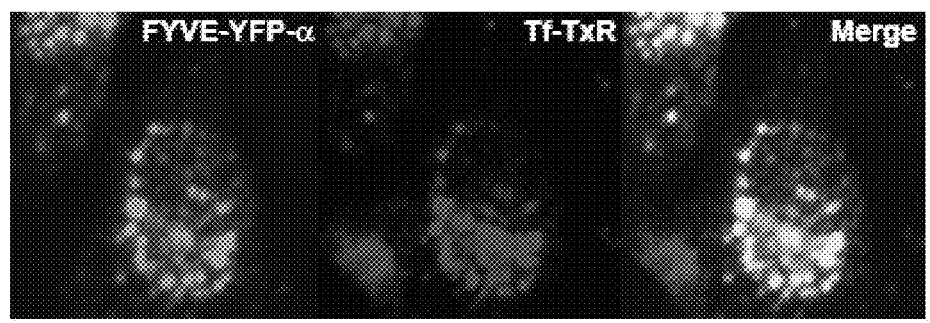
FIG. 5. Localization of endofin FYVE-eYFP-α (green) to endosomes, visualized by TexasRed-conjugated transferrin localization (Tf-TxR, red).

In order to design the endosomal probe, we took advantage of the fact that the cytosolic face of endosomes is enriched in the phospholipid phosphatidylinositol-3-phosphate (PI-3P) to which FYVE domain-containing proteins bind (Blatner et al. (2004) The molecular basis of the differential subcellular localization of FYVE domains. *J Biol Chem* 279, 53818-53827). We screened several FYVE domains for this purpose, specifically that of Fens, EEA1, and Endofin; the localization of FYVE domain fusions to YFP-α peptide constructs is shown in FIG. 1b, along with several endosomally-localized rab GTPases for comparison. Several of the FYVE domains show punctuate staining indicative of endosomal localization. The endofin FYVE domain showed the clearest localization, as expected based on previous studies (Seet, L. F., and Hong, W. (2001) Endofin, an endosomal FYVE domain protein. *J Biol Chem* 276, 42445-42454). The endosomal label transferrin was used to validate that the punctuate staining pattern exhibited by the endofin FYVE-eYFPα fusion specifically labeled endosomes; the extensive colocalization of the red transferrin signal and green eYFP signal confirmed the almost complete localization of endofin-FYVE to endosomes (FIG. 5).

Figure 3:
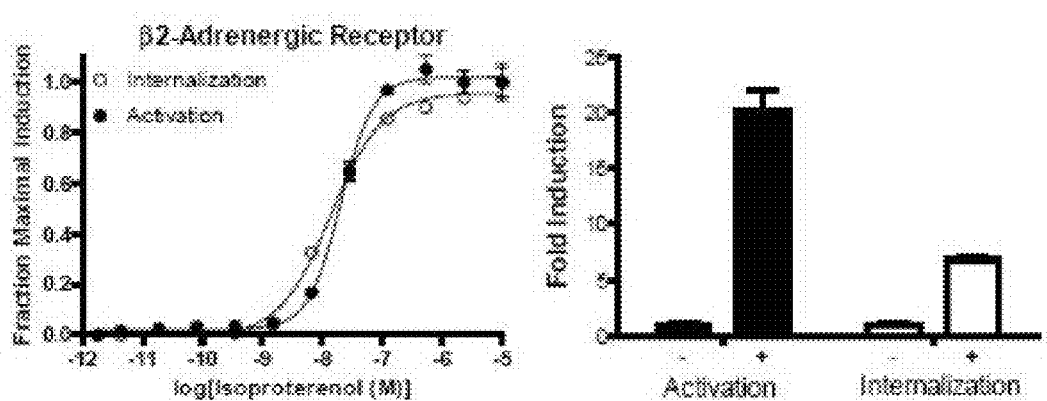
FIG. 3. Dose response of various GPCRs in the internalization assay (FYVE-ω+GPCR-eYFP-α, open circles) and activation assay (β-arrestin-ω+GPCR-eYFP-α, filled circles). Left panels show dose-response with values normalized to 0 (lowest dose) and 1 (highest dose); right panels show fold induction of unstimulated cells, normalized to 1, compared to highest dose shown in left panels. (a) Dose response and fold induction of β2-adrenergic receptor assays to the small molecule agonist isoproterenol at 1 h. (b) Dose response and fold induction of angiotensin receptor 1a receptor assays to the peptide ligand angiotensin II at 2 hr. (c) Dose response and fold induction of the Arg-vasopressin receptor assays to the peptide ligand Arg-vasopressin at 2 hr. (d) Dose response and fold induction of the somatostatin 2 receptor assays to the peptide ligand somatostatin-14 at 2 hr. Error bars represent standard deviations of 2-4 biological replicates; also shown in left panels are best-fit sigmoidal dose-response curves.
Figure 3:
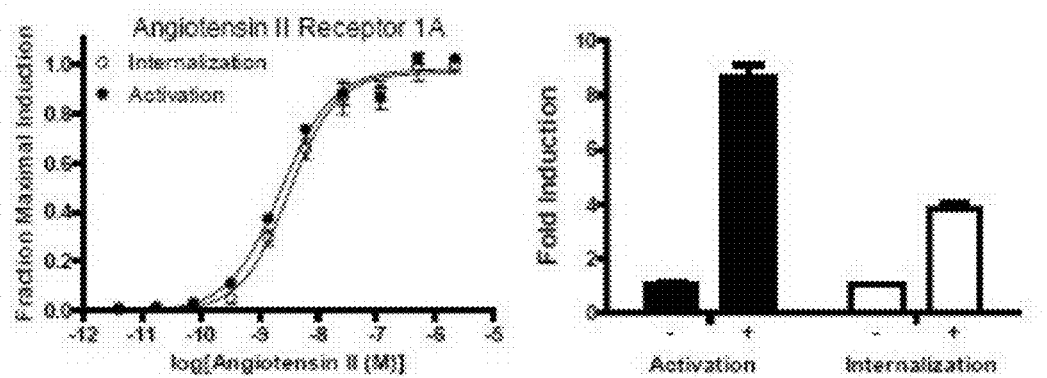
Figure 3:
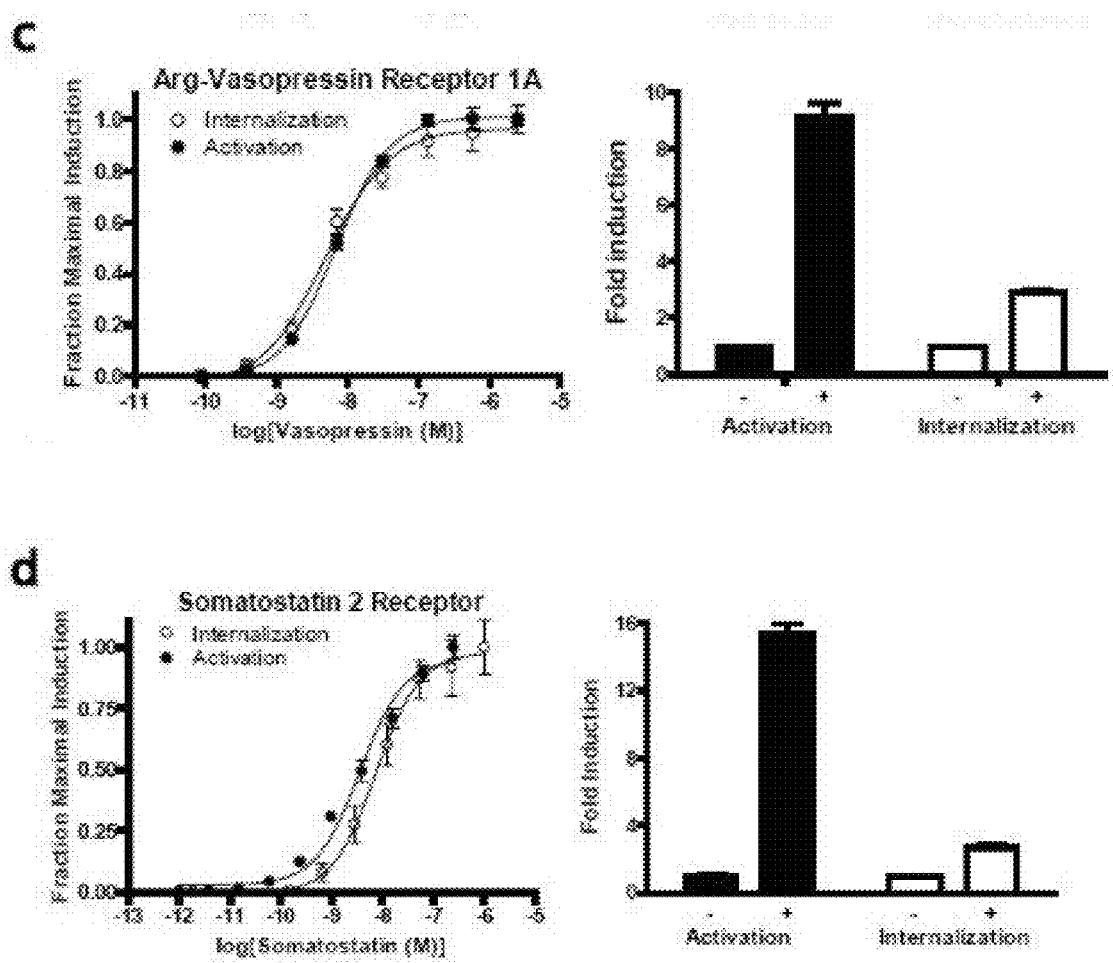

C2C12 cells expressing the endofin FYVE-eYFP-α construct were transduced with a construct encoding a C-terminal fusion of β2AR with the ω-fragment (β2AR-ω). The resulting assay cell line was treated with isoproterenol, and β-galactosidase activity was measured in 96-well dishes using a chemiluminescent substrate. Agonist treatment resulted in a 6-fold induction of β-gal activity by 1 hour of stimulation (FIG. 1c). These results demonstrate that our complementation-based internalization assay could measure GPCR internalization. The time course of increased β-gal activity shows that this process reaches a plateau by 1 hour of stimulation. The internalization of β2AR to endosomes was confirmed by intracellular localization and colocalization with transferrin (FIG. 1c and data not shown). As a second test of the system, we generated a dose-response curve by treating the cells with isoproterenol and measuring β-gal activity at 60 minutes (FIG. 1d, 3a). We obtained an $EC_{50}$ of 20 nM, which is in line with previous studies of B2AR activation (Wangemann et al. (1999) Beta1-adrenergic receptors but not beta2-adrenergic or vasopressin receptors regulate K+ secretion in vestibular dark cells of the inner ear. *J Membr Biol* 170, 67-77), showing that the assay can be used as a quantitative measure of GPCR activation/internalization.

The canonical pathway for GPCR internalization involves the binding of a β-arrestin molecule that bridges the GPCR and the internalization machinery. Previously, we developed a complementation assay for the interaction of a GPCR and β-arrestin (Wehrman et al. (2006) A system for quantifying dynamic protein interactions defines a role for Herceptin in modulating ErbB2 interactions. *Proc Natl Aced Sci USA* 103, 19063-19068; and von Degenfeld, et al., in preparation). The development of the internalization assay affords the ability to quantitatively compare GPCR internalization and β-arrestin binding. To compare the results of the internalization assay and the GPCR activation assay, we measured the dose-response of the two assays in parallel; the dose-response curves yielded $EC_{50}$s of 14 nM (activation) and 20 nM (internalization), in agreement with a previously reported value of 14 nM (FIG. 1d, 3a) (Wehrman et al. (2006) A system for quantifying dynamic protein interactions defines a role for Herceptin in modulating ErbB2 interactions. *Proc Natl Aced Sci USA* 103, 19063-19068).

Quantitative modulation of βAR activation and internalization. As noted above, we monitored the time responsiveness of both β2AR assays. Internalization of the β2AR began to plateau at 1 hr, while receptor activation continued to increase up to 2 hr (FIG. 1c and data not shown). This time-course was confirmed by imaging fluorescent receptor fusions, which showed translocation of the receptor from the plasma membrane to punctate intracellular vesicles (FIG. 1c). Both assays could be inhibited by the β2AR antagonist propranolol (FIG. 2a), with an $IC_{50}$ value of 38 nM in the presence of 10 μM isoproterenol, in agreement with published reports (Davis et al. (1990) Beta-adrenergic receptors on human tracheal epithelial cells in primary culture. *Am J Physiol* 258, C71-76). These results show that both the internalization and activation assays can be used to assay modulators of GPCR activity.

To determine whether the activation and internalization assays could be uncoupled, we tested the effects of temperature on the internalization and activation of the β2AR. In particular, it has been described that low temperatures inhibit internalization (Vasile et al. (1983) Visualization of the binding, endocytosis, and transcytosis of low-density lipoprotein in the arterial endothelium in situ. *J Cell Biol* 96, 1677-1689), and detailed studies have demonstrated that a drop to 16° C. is sufficient to prevent internalization (Wolkers et al. (2003) Temperature dependence of fluid phase endocytosis coincides with membrane properties of pig platelets. *Biochim*

Figure 2:
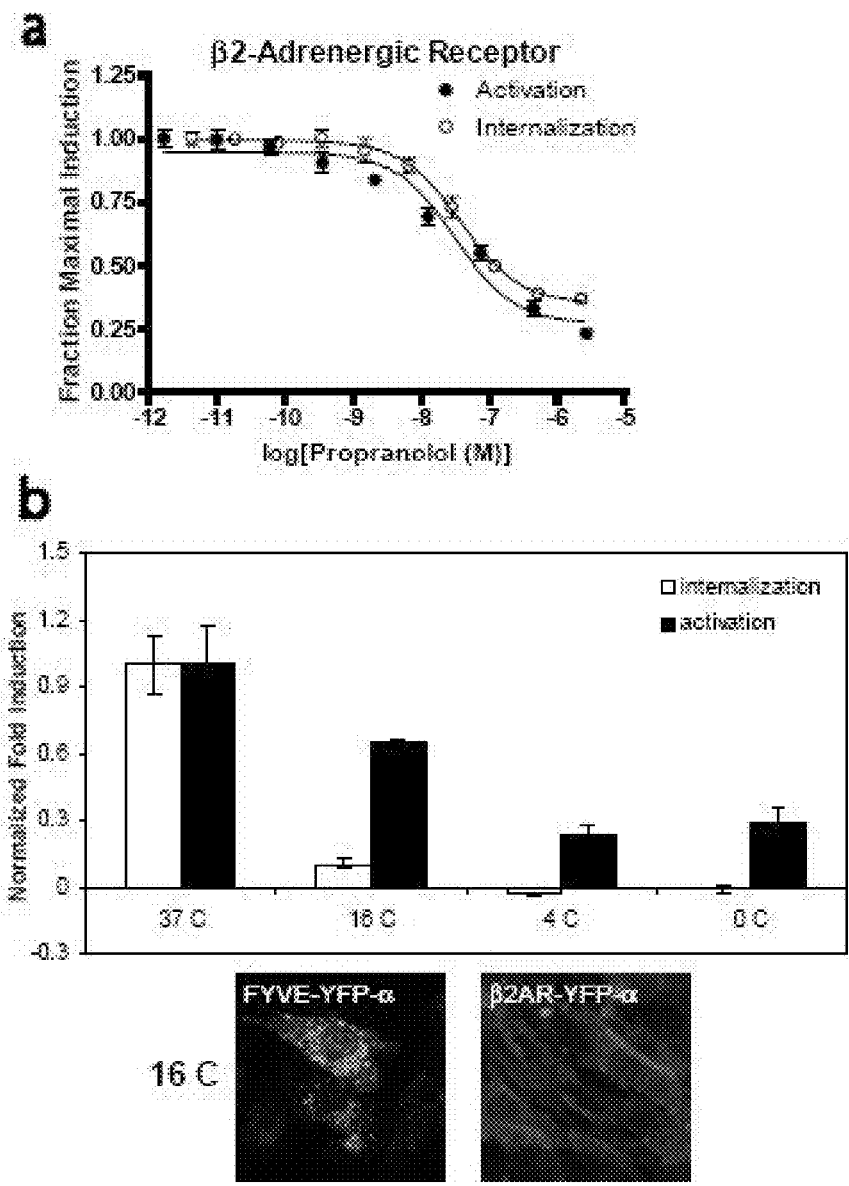
FIG. 2. Characterization of β2-Adrenergic Receptor (β2AR) Assays. (a) Inhibition of β2AR activation and internalization by the competitive antagonist propranolol, in the presence of 10 μM isoproterenol. (b) Low-temperature selective inhibition of β2AR internalization; top panel shows complementation assay results, while bottom panel shows confirmation by fluorescence of YFP fusion proteins. Error bars represent standard deviations of biological replicates, and curves show best-fit sigmoidal dose-response curves.

*Biophys Acta* 1612, 154-163). In agreement with these findings, at temperatures below 16° C. the β2AR internalization was inhibited relative to activation (FIG. 2b). Fluorescent imaging confirmed these results, showing no effect on FYVE domain localization but a lack of β2AR internalization at 16° C. (FIG. 2b, bottom panels). As expected, the activation assay continued to function at temperatures as low as 0° C., although the magnitude of induction was reduced.

Generalization of receptor activation and internalization assays. Upon ligand binding most classes of GPCRs are internalized. To determine the applicability of the assay to different GPCRs, we tested if the internalization assay could be used to detect the internalization of the Angiotensin II 1a (AT1a), Arginine-vasopressin 1a (AVPR1a), and Somatostatin 2 receptors. Using the Angiotensin II receptor 1a (AT1a), we observed a 4-fold increase in activity with the internalization assay with an $EC_{50}$ of 3.3 nM, close to the value of 1.2 nM reported in the literature for $IP_3$ production (Conchon et al. (1997) The C-terminal third intracellular loop of the rat AT1A angiotensin receptor plays a key role in G protein coupling specificity and transduction of the mitogenic signal. *J Biol Chem* 272, 25566-25572) (FIG. 3b). When we employed the arrestin-binding activation assay for this receptor, we obtained an 8.5-fold increase in enzyme activity and an $EC_{50}$ of 2.4 nM. Similarly robust results were obtained with the Arginine-vasopressin receptor 1a (AVPR1a) in response to vasopressin: the internalization assay resulted in an approximately 4-fold induction with an $EC_{50}$ of 4.4 nM, and the arrestin assay yielded approximately 9-fold induction with an $EC_{50}$ of 6 nM (activation) (FIG. 3c). With the Somatostatin 2 receptor in response to somatostatin-14, a 3-fold induction and 7 nM $EC_{50}$ was observed using the internalization assay and 14-fold induction and 3 nM $EC_{50}$ with the arrestin assay (FIG. 3d). These results show that the internalization assay yields 3-fold or better inducibility, with relatively low error.

Figure 4:
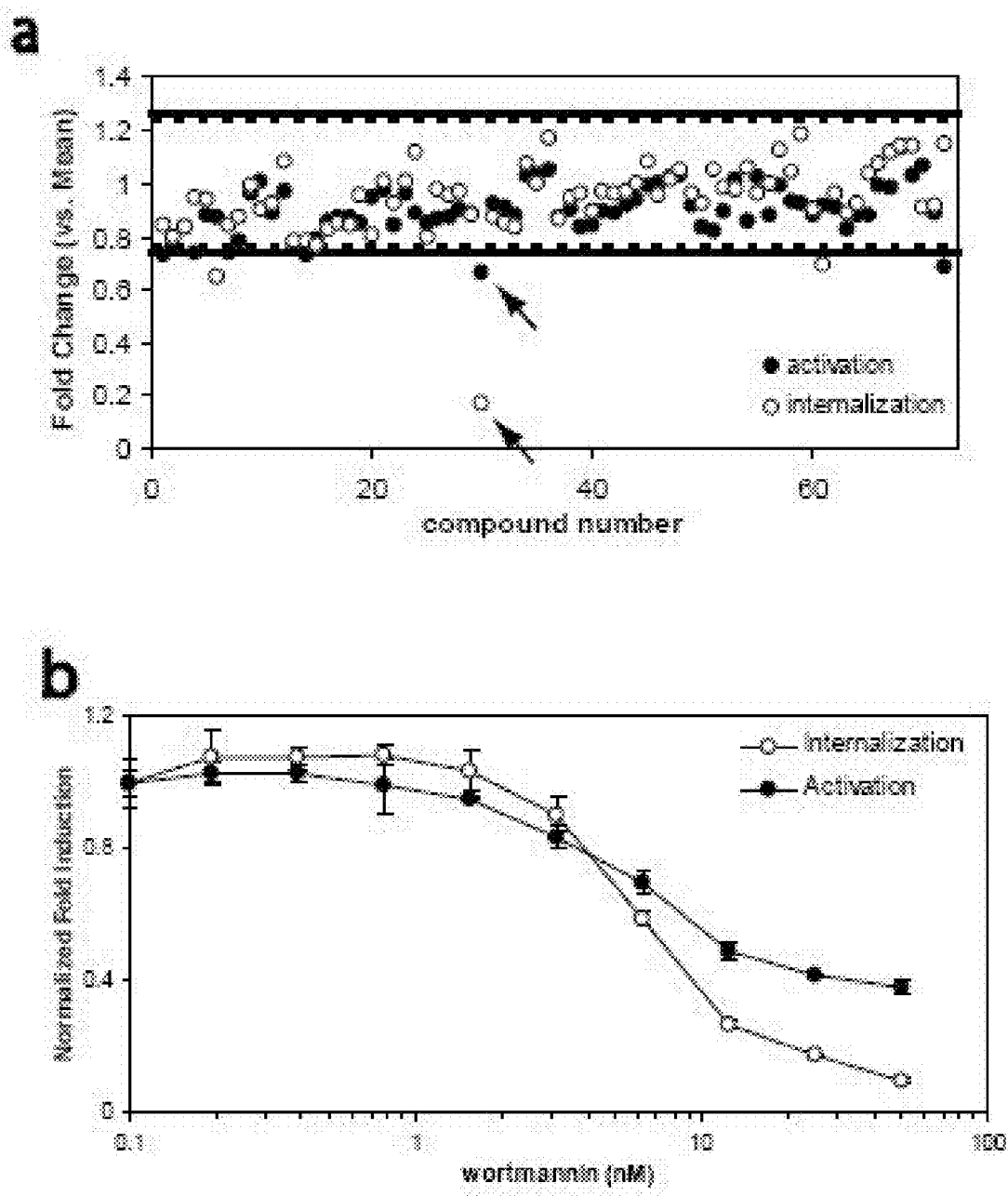
FIG. 4. (a) Results of a small-scale screen of Biomol's Kinase/Phosphatase Inhibitor Library at 3 uM. Compounds are arranged along the x-axis, and normalized signal is plotted on the y-axis. Signals were averaged between duplicates and then normalized so that positive controls were 1 and negative controls were 0; horizontal bars represent twice the standard deviation (solid, activation assay; broken, internalization assay). Arrows denote data points corresponding to the compound wortmannin (number 30). (b) Dose response curve for wortmannin; compound was applied 30 min before stimulation with 10 uM isoproterenol. Error bars represent standard deviation of triplicates. (c) Fluorescence of stimulated β2AR-YFP (top row) and FYVE-YFP (bottom row) in the presence of 1% DMSO or 1 μM wortmannin.
Figure 4:
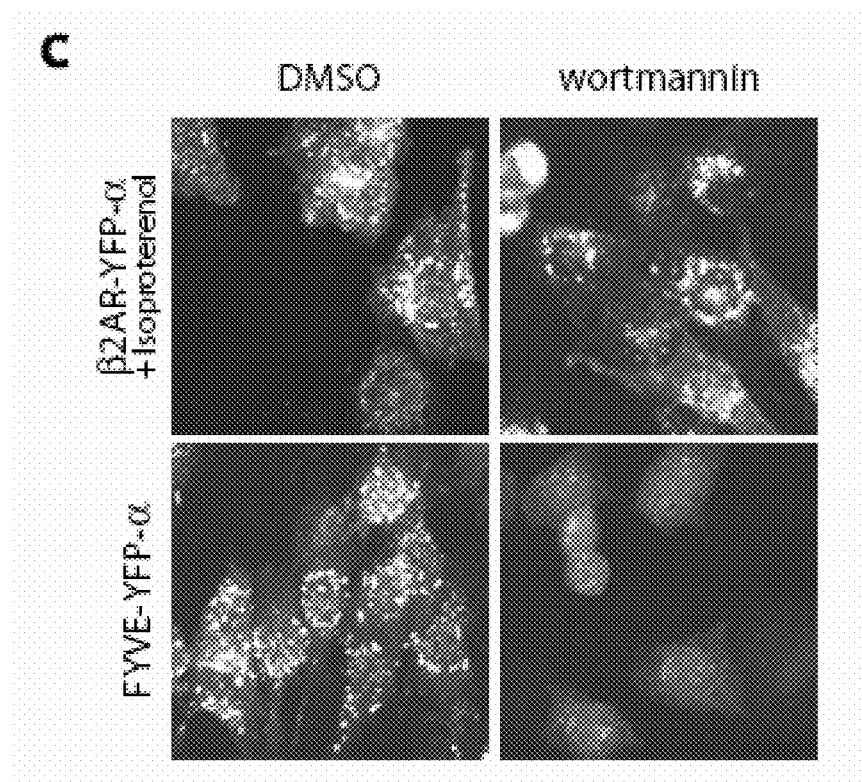

High-throughput screen. Given that our set of assays displayed a robust response with low noise, we proceeded to test them in a high-throughput setting. For this trial, we selected a kinase/phosphatase inhibitor library (BIOMOL International, Plymouth Meeting, Pa.) and performed the assay in a 384-well plate in duplicate. FIG. 4a shows the results of the screen, with the assays yielding a Z-factor of 0.6 in this setting; horizontal lines show twice the standard deviation away from the mean. The screen yielded wortmannin, a phosphatidylinositol 3-kinase inhibitor, as a significant hit (arrows in FIG. 4a), which was confirmed by a separate dose-response curve (FIG. 4b). As expected, wortmannin's inhibition of PI-3-kinase depleted the PI-3P levels on endosomes; as FYVE domains employ this phospholipid for their localization, we would expect a loss of specific endosomal localization. Indeed, we did observe that the endofin FYVE-GFP-α probe relocalized to the cytoplasm upon treatment of cells with wortmannin (FIG. 4c and Ridley et al. (2001) FENS-1 and DFCP1 are FYVE domain-containing proteins with distinct functions in the endosomal and Golgi compartments. *J Cell Sci* 114, 3991-4000). Thus, wortmannin would be expected to prevent colocalization, and therefore complementation, of the endosomal marker and internalized receptors to yield a consequent decrease in the internalization assay signal. Although wortmannin appeared to inhibit the activation by approximately 50%, the effects on the internalization assay were more pronounced with an approximately 90% inhibition. In addition to wortmannin, we also discovered two more inhibitors of internalization; these were staurosporine and erbstatin, both kinase inhibitors.

The data above demonstrate that we can quantitatively measure both a receptor activation-dependent protein-protein interaction and an internalization-dependent colocalization event using the assay system and methods described herein. Such systems and methods find use in numerous applications, including investigating biological questions, e.g., the regulation of receptor internalization, or in high-throughput screens, in which a library of compounds can be assayed for effects on protein localization simultaneously. As such, the present invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of detecting translocation of a cell-surface receptor to an endosome, said method comprising:
   (a) providing a cell comprising:
      (i) a first fusion protein comprising a cell-surface receptor and a first β-galactosidase fragment; and
      (ii) a second fusion protein comprising an endofin FYVE domain that localizes to a phosphatidylinositol-3-phosphate-containing endosome and a second β-galactosidase fragment; wherein said first and second β-galactosidase fragments complement one another to produce an active β-galactosidase enzyme when in close proximity, and the second β-galactosidase fragment is altered by an amino acid substitution in a region from amino acid residue 29 to 41 of the wild-type β-galactosidase sequence such that the first and second β-galactosidase fragments have a reduced affinity for each other as compared to wild type fragments; and
   (b) evaluating said cell for active β-galactosidase activity to detect translocation of said cell-surface receptor to said endosome.

2. The method according to claim 1, wherein said providing comprises introducing nucleic acids encoding said first and second fusion proteins into said cell.

3. The method according to claim 1, wherein said method further comprises contacting said cell with an agent prior to said evaluating.

4. The method according to claim 3, wherein said agent is selected from one or more of: ligand for said cell-surface receptor, antagonist of said cell-surface receptor, test compound, candidate therapeutic agent, candidate ligand or agonist of said cell-surface receptor, candidate antagonist of said cell-surface receptor.

5. The method according to claim 3, wherein said method further comprises evaluating β-galactosidase activity before and after said contacting.

6. The method according to claim 1, wherein said cell surface receptor is a G protein coupled receptor (GPCR).

7. The method according to claim 1, wherein said cell surface receptor is selected from the group consisting of: cytokine receptor, chemokine receptor, and antigen receptor.

8. The method according to claim 1, wherein said cell is a mammalian cell.

9. The method according to claim 1, wherein said cell is a yeast cell.

10. The method according to claim 1, wherein said second β-galactosidase fragment is a variant minimal N-terminal β-galactosidase peptide.

11. The method according to claim 10, wherein said variant minimal N-terminal β-galactosidase peptide comprises at least one amino acid variation as compared to a β-galactosidase fragment consisting of amino acids 3 to 92 of *E. coli* wild type β-galactosidase.

12. The method according to claim 10, wherein said second β-galactosidase fragment is a deletion mutant of the wild type *E. coli* β-galactosidase protein.

13. The method according to claim 12, wherein said deletion mutant is selected from: the M15 acceptor fragment and the M112 dimer.

14. The method according to claim 1, wherein said evaluating step occurs in vivo.

* * * * *